United States Patent
Yamada et al.

(10) Patent No.: US 9,724,228 B2
(45) Date of Patent: Aug. 8, 2017

(54) NASAL CAVITY INSERTION DEVICE FIXTURE AND NASAL CAVITY INSERTION DEVICE SET INCLUDING THE SAME

(75) Inventors: Hiroshi Yamada, Otsu (JP); Yosuke Taniguchi, Otsu (JP); Yoshiki Hattori, Otsu (JP); Kenji Hioki, Otsu (JP); Shinichi Sakane, Otsu (JP)

(73) Assignee: seven dreamers laboratories, Inc., Tokyo (JP)

(*) Notice: Subject to any disclaimer, the term of this patent is extended or adjusted under 35 U.S.C. 154(b) by 0 days.

(21) Appl. No.: 13/582,630

(22) PCT Filed: Mar. 4, 2011

(86) PCT No.: PCT/JP2011/001286
§ 371 (c)(1),
(2), (4) Date: Sep. 4, 2012

(87) PCT Pub. No.: WO2011/108282
PCT Pub. Date: Sep. 9, 2011

(65) Prior Publication Data
US 2012/0325223 A1    Dec. 27, 2012

(30) Foreign Application Priority Data

Mar. 5, 2010 (JP) ................ 2010-049339
Sep. 3, 2010 (JP) ................ 2010-197664

(51) Int. Cl.
A61F 5/56       (2006.01)
A61M 39/10     (2006.01)
(Continued)

(52) U.S. Cl.
CPC ........... *A61F 5/56* (2013.01); *A61M 16/0461* (2013.01); *A61M 31/00* (2013.01); *A61M 39/10* (2013.01);
(Continued)

(58) Field of Classification Search
CPC . A61F 5/08; A61F 5/56; A61M 29/00; A61M 31/00; A61M 16/0461; A61M 39/00; A61M 39/10
(Continued)

(56) References Cited

U.S. PATENT DOCUMENTS 1,014,758 A * 1/1912 Knowlson ............. 606/199
2,264,153 A * 11/1941 Rowe ................. 128/204.12
(Continued)

FOREIGN PATENT DOCUMENTS

FR       892937 A       5/1944
FR       2631229 A1    11/1989
(Continued)

OTHER PUBLICATIONS

International Search Report for PCT/JP2011/001286 dated Apr. 12, 2011.
(Continued)

*Primary Examiner* — Keri J Nelson
(74) *Attorney, Agent, or Firm* — Hamre, Schumann, Mueller & Larson, P.C.

(57) ABSTRACT

A fixture is provided for attachment to a device to be inserted into a nasal cavity. Further, the fixture is a nasal cavity insertion device fixture formed of a wire rod. The fixture includes a first wire rod part, a second wire rod part, and a third wire rod part. The second wire rod part is connected to the first wire rod part and formed by folding back the wire rod so as to be opposed to the first wire rod part. The third wire rod part is connected to the second wire rod part and formed by bending the wire rod so as to be disposed oppositely to a side of the second wire rod part facing the first wire rod part.

11 Claims, 21 Drawing Sheets

(51) Int. Cl.
  *A61M 31/00* (2006.01)
  *A61M 16/04* (2006.01)
  *A61M 29/00* (2006.01)
(52) U.S. Cl.
  CPC ......... *A61M 16/0488* (2013.01); *A61M 29/00* (2013.01); *A61M 2210/0618* (2013.01)
(58) Field of Classification Search
  USPC .... 128/848, 200.26, 204.12, 206.11, 207.18; 606/199
  See application file for complete search history.

(56) References Cited

U.S. PATENT DOCUMENTS

| | | | |
|---|---|---|---|
| 2,426,161 | A | 8/1947 | Biederman |
| 2,672,138 | A | 3/1954 | Carlock |
| 3,568,678 | A | 3/1971 | Pourquier et al. |
| 5,097,827 | A | 3/1992 | Izumi |
| 5,727,543 | A * | 3/1998 | Corsaro ................ A61M 29/00 128/200.24 |
| 2003/0195552 | A1* | 10/2003 | Santin ........................... 606/199 |
| 2005/0121036 | A1 | 6/2005 | Tohara |
| 2006/0266367 | A1* | 11/2006 | Noce ........................ 128/207.18 |
| 2007/0277831 | A1* | 12/2007 | Luhrs ................... A61M 25/02 128/207.18 |
| 2009/0062927 | A1 | 3/2009 | Marten et al. |
| 2009/0248058 | A1 | 10/2009 | Kotler |
| 2009/0266365 | A1 | 10/2009 | Oberle |
| 2010/0030252 | A1 | 2/2010 | Stewart |
| 2010/0063532 | A1* | 3/2010 | Moore ......................... 606/199 |

FOREIGN PATENT DOCUMENTS

| | | |
|---|---|---|
| GB | 191504148 A | 12/1915 |
| GB | 191504148 A | 12/1915 |
| JP | 56-25619 Y2 | 6/1981 |
| JP | S56-025619 Y | 6/1981 |
| JP | 2002-301152 | 10/2002 |
| JP | 2005-087683 | 4/2005 |
| JP | 2006-204630 | 8/2006 |
| JP | 2006-341050 A | 12/2006 |
| JP | 2008-504090 | 2/2008 |
| JP | 2008-149089 | 7/2008 |
| JP | 2008-149089 A | 7/2008 |
| JP | 2009-034384 | 2/2009 |
| JP | 2009-072581 | 4/2009 |
| JP | 2009-072581 A | 4/2009 |
| JP | 2009-072582 | 4/2009 |
| JP | 2009-532159 | 9/2009 |
| WO | 98-23233 | 6/1998 |
| WO | 2008/058367 | 5/2008 |

OTHER PUBLICATIONS

PCT International Preliminary Report on Patentability, Mar. 29, 2012.

European Search Report dated Jul. 18, 2014, issued in corresponding European application.

* cited by examiner (a)

(b)

(c)

(d)

NASAL CAVITY INSERTION DEVICE FIXTURE AND NASAL CAVITY INSERTION DEVICE SET INCLUDING THE SAME

CROSS-REFERENCE TO RELATED APPLICATIONS

This U.S. National Stage Application claims priority under 35 U.S.C. §119(a) to Japanese Patent Application No. 2010-049339, filed in Japan on Mar. 5, 2010, and Japanese Patent Application No. 2010-197664, filed in Japan on Sep. 3, 2010. The entire disclosures of Japanese Patent Application Nos. 2010-049339 and 2010-197664 are hereby incorporated herein by reference.

BACKGROUND OF THE INVENTION

Field of the Invention

The present invention relates to a nasal cavity insertion device fixture and a nasal cavity insertion device set including the same.

Description of the Related Art

Patients of obstructive sleep apnea syndrome (OSAS) intermittently repeat a temporally suffocated state (apnea, infrequent breathing) while the pharynx of the upper respiratory tract is obstructed due to a complication of muscle relaxation and obesity and the like during sleep. Therefore, patients of OSAS are suffered from hypertension or disorders in brain blood vessels and cardiac blood vessels. Further, patients of OSAS cannot sleep sufficiently, and therefore, tend to feel drowsy in the daytime and/or tend to lack of concentration or vitality in the daytime. Yet further, when driving a car, patients of OSAS have high chances of causing an accident, a serious accident or the like due to falling asleep at the wheel.

On the other hand, similarly to OSAS, snoring occurs when the respiratory tract's mucus membranes of the pharynx and the like vibrate due to stenosis or obstruction of the upper respiratory tract during sleep. Snoring disturbs not only the sleep of a roommate but also the sound sleep of a snorer oneself with the sound, and the snorer tends to feel drowsy in the daytime or tends to lack of concentration or vitality in the daytime.

The aforementioned "obstructive speed apnea syndrome" and "snoring syndrome" will be hereinafter collectively referred to as "sleep disorder".

In view of the above, a variety of proposals have been made in recent years for treating or resolving OSAS. For example, such proposals include "a method of inserting a tube for resolving OSAS into the pharynx via a nasal passage (e.g., Japan Laid-open Patent Application Publication No. JP-A-2009-072581)", "a method of expanding the pharynx by inserting a tube, to the tip of which a water swelling resin is applied, into the pharynx via a nasal passage, and subsequently, by swelling the water swelling resin using moisture in the periphery of the pharynx (see e.g., Japan Laid-open Patent Application Publication No. JP-A-2009-072581)", "a method of expanding the pharynx by inserting a tube for resolving OSAS, which has an expansion portion in the tip thereof, into the pharynx via a nasal passage, and subsequently, by expanding the expansion portion through a user's operation (see e.g., Japan Laid-open Patent Application Publications Nos. JP-A-2006-204630, JP-A-2009-034384, JP-A-2009-072581, JP-A-2009-072582, etc.)" and etc.

SUMMARY OF THE INVENTION

Incidentally, in the aforementioned methods, it has been concerned that a patient of sleep disorder is not treated sufficiently due to the displacement or the detachment of the nasal cavity insertion tube during the sleep of the patient of sleep disorder.

It is an object of the present invention to provide a nasal cavity insertion device fixture and a nasal cavity insertion device set including the same, whereby the displacement or the detachment of a nasal cavity insertion tube can be prevented during the sleep of a patient of sleep disorder.

A nasal cavity insertion device fixture according to a first aspect of the present invention fixes a device to be inserted into a nasal cavity.

According to the aforementioned configuration, the nasal cavity insertion device fixture can fix the aforementioned device. Therefore, the nasal cavity insertion device fixture can prevent the displacement or the detachment of the device during the sleep of a patient of sleep disorder.

A nasal cavity insertion device fixture according to a second aspect of the present invention relates to the nasal cavity insertion device fixture according to the first aspect. The present nasal cavity insertion device fixture fixes the device through contact with an inside or an outside of a nasal passage.

According to the aforementioned configuration, the device can be fixed by means of the force that the nasal cavity insertion device fixture makes by contacting with the inside or the outside of a nasal passage. Therefore, the displacement or the detachment of the device can be prevented during the sleep of a patient of sleep disorder.

Further, the nasal cavity insertion device fixture is attached to a nose. Therefore, a user can attach the nasal cavity insertion device fixture for oneself.

A nasal cavity insertion device fixture according to a third aspect of the present invention includes: a first insertion part to be inserted into one nasal passage; a second insertion part to be inserted into the other nasal passage; and a coupling part coupling the first insertion part and the second insertion part so that the bridge of the nose is pressed from the both sides thereof by the first insertion part and the second insertion part.

According to the aforementioned configuration, the bridge of the nose can be clipped by the first insertion part and the second insertion part. The device can be thereby firmly fixed. Therefore, the displacement or the detachment of the device can be prevented during the sleep of a patient of sleep disorder.

A nasal cavity insertion device fixture according to a fourth aspect of the present invention relates to the nasal cavity insertion device fixture according to the third aspect, and wherein either the first insertion part or the second insertion part has a plate shape, a tubular shape or a spring shape.

According to the aforementioned configuration, either the first insertion part or the second insertion part, having a plate shape, a tubular shape or a spring shape, can make contact with the inside of a nasal passage. The device can be thereby firmly fixed. Therefore, the displacement or the detachment of the device can be prevented during the sleep of a patient of sleep disorder.

Further, in using either the first insertion part or the second insertion part that has a plate shape, either the first insertion part or the second insertion part, having a plate shape, makes surface contact with the inside of a nasal passage. Therefore, the displacement or the detachment of the device can be further prevented. In addition to this, a contact area with the nasal cavity insertion device fixture is increased within the nasal passage. Therefore, pain in the bridge of the nose can be relieved.

Alternatively, in using either the first insertion part or the second insertion part that has either a tubular shape or a spring shape, an air flow path can be reliably produced even when either the first insertion part or the second insertion part is disposed in a nasal passage. Accordingly, obstruction of breathing can be prevented by either the first insertion part or the second insertion part disposed in the nasal passage. In addition to this, a contact area with the nasal cavity insertion device fixture is increased within the nasal passage. Therefore, pain in the bridge of the nose can be relieved.

Yet alternatively, in using the first insertion part having a spring shape, the first insertion part can be inserted into a nasal cavity while the spring is compressed even when the nasal cavity length is short. Therefore, the first insertion part is not required to be cut or the like in accordance with the nasal cavity length.

A nasal cavity insertion device fixture according to a fifth aspect of the present invention relates to the nasal cavity insertion device fixture according to the third aspect or the fourth aspect, and wherein either the first insertion part or the second insertion part is extended from the nasal passage to a pharynx.

According to the aforementioned configuration, the device can be carried to an affected part (pharynx) using either the first insertion part or the second insertion part extended from a nasal passage to the pharynx. Therefore, the device is not required to be extended from a nasal passage to the pharynx. Accordingly, a device can be used that has a size enough to expand the affected part (pharynx).

A nasal cavity insertion device fixture according to a sixth aspect of the present invention includes: a contact part making contact with either an inside or an outside of a nasal passage; and a connecting part connecting the contact part and a device to be inserted into a nasal cavity.

According to the aforementioned configuration, the nasal cavity insertion device fixture can fix the device by means of the contact force of the contact portion making contact with either the inside or the outside of a nasal passage. Therefore, the nasal cavity insertion device fixture can prevent the displacement or the detachment of the device during the sleep of a patient of sleep disorder.

A nasal cavity insertion device fixture according to a seventh aspect of the present invention relates to the nasal cavity insertion device fixture according to the sixth aspect, and wherein the contact part includes a clip part clipping a bridge of a nose.

According to the aforementioned configuration, the bridge of the nose can be clipped with the nasal cavity insertion device fixture. The device can be thereby firmly fixed. Therefore, the displacement or the detachment of the device can be prevented during the sleep of a patient of sleep disorder.

Further, the attachment position of the nasal cavity insertion device fixture is set to be a nose (a bridge of the nose). Therefore, a user can attach the nasal cavity insertion device fixture for oneself.

A nasal cavity insertion device fixture according to an eighth aspect of the present invention relates to the nasal cavity insertion device fixture according to any one of the third to seventh aspects. The present nasal cavity insertion device fixture further includes a hook part hooked on a nasal wing.

According to the aforementioned configuration, the device can be further fixed at the nasal wing. Accordingly, the displacement or the detachment of the device can be effectively prevented.

A nasal cavity insertion device fixture according to a ninth aspect of the present invention is a nasal cavity insertion device fixture formed by a wire rod, and includes a first wire rod part, a second wire rod part and a third wire rod part. It should be noted that the term "wire rod" herein may refer to a round wire, a flat rectangular wire or a thin flat rectangular wire. Further, the material forming the nasal cavity insertion device fixture is not particularly limited, but may be, for instance, metal, resin or etc. The second wire rod part is continued to the first wire rod part. Further, the second wire rod part is formed by folding back the wire rod so that the second wire rod part is opposed to the first wire rod part . The third wire rod part is continued to the second wire rod part . Further, the third wire rod part is formed by bending the wire rod so that the third wire rod part is disposed oppositely to a first wire rod part formed side of the second wire rod part.

A method of using the present nasal cavity insertion device fixture will be hereinafter explained.

First, the tip portion of the third wire rod part is pierced into the base end side sidewall of the device. Under the condition, the device is then inserted from its tip side into a nasal passage and the tip portion of the device is gradually inserted toward the pharynx. Then finally, the tip portion of the device is inserted into the pharynx while the bottom end of the bridge of the nose is clipped with a portion of the second wire rod part and the first wire rod part. It should be herein noted that the tip of the first wire rod part exists within the nasal passage.

Therefore, the present nasal cavity insertion device fixture can firmly fix the device to the bridge of the nose. Therefore, the present nasal cavity insertion device fixture can prevent the displacement or the detachment of the device during the sleep of a patient of OSAS or snoring syndrome.

A nasal cavity insertion device fixture according to a tenth aspect of the present invention relates to the nasal cavity insertion device fixture according to the ninth aspect, and wherein the third wire rod part is continued to the second wire rod part . Further, the third wire rod part is formed by folding back the wire rod in a direction oppositely to the second wire rod part so that the third wire rod part is opposed to the second wire rod part on an opposite side of the first wire rod part formed side of the second wire rod part.

Therefore, the device can be clipped with the second wire rod part and the third wire rod part . Accordingly, the present nasal cavity insertion device fixture can prevent the detachment of the device from the nasal cavity insertion device fixture during the sleep of a patient of OSAS or snoring syndrome.

A nasal cavity insertion device fixture according to an eleventh aspect of the present invention relates to the nasal cavity insertion device fixture according to the tenth aspect, and wherein the third wire rod part has a wavy shape.

Therefore, in clipping the sidewall of the device with the third wire rod part and a portion of the second wire rod part, less contact portions are produced between the sidewall of the device and the third wire rod part. Therefore, a patient of sleep disorder can easily perform a work of clipping the sidewall of the device with the third wire rod part and a portion of the second wire rod part.

A nasal cavity insertion device fixture according to a twelfth aspect of the present invention relates to the nasal cavity insertion device fixture according to the tenth aspect or the eleventh aspect. The present nasal cavity insertion device fixture further includes a fourth wire rod part. The fourth wire rod part is continued to the third wire rod part. Further, the fourth wire rod portion is formed by folding back the wire rod in a direction oppositely to the third wire rod part so that the fourth wire rod part is opposed to the third wire rod part on an opposite side of a second wire rod part formed side of the third wire word part.

A method of using the present nasal cavity insertion device fixture will be hereinafter explained.

First, the tip portion of the fourth wire rod part is pierced through the base end side section of the device, and then, the device is moved to the folded-back section between the second wire rod part and the third wire rod part. Under the condition, the device is then inserted from its tip side into a nasal passage, and the tip portion of the device is gradually inserted toward the pharynx. Then, finally, the tip portion of the device is inserted into the pharynx, while the bottom end of the bridge of the nose is clipped with a portion of the second wire rod part and the first wire rod part. Further, the folded-back section between the third wire rod part and the fourth wire rod part is herein disposed astride either of the nasal wings.

Thus, in the present nasal cavity insertion device fixture, the hook part is disposed on either of the nasal wings. Therefore, the present nasal cavity insertion device fixture can prevent the device from being inserted into a nasal passage or the body more than necessity during the sleep of a patient of sleep disorder.

A nasal cavity insertion device fixture according to a thirteenth aspect of the present invention relates to the nasal cavity insertion device fixture according to any one of the ninth to twelfth aspects, and wherein the first wire rod part and the second wire rod part are formed by first opposed portions, second opposed portions and third opposed portions. The first opposed portions are separated at a first distance. In other words, in the first opposed portions, a portion of the first wire rod part and a portion of the second wire rod part are separated by the first distance. The second opposed portions are continued to the first opposed portions. Further, the second opposed portions are separated at a second distance shorter than the first distance. In other words, in the second opposed portions, another portion of the first wire rod part and another portion of the second wire rod part are separated by the second distance. The third opposed portions are continued to the second opposed portions. Further, the third opposed portions are separated at a third distance longer than the second distance. In other words, in the third opposed portions, yet another portion of the first wire rod part and yet another portion of the second wire rod part are separated by the third distance.

Therefore, in the present nasal cavity insertion device fixture, a constricted section is formed by the first wire rod part and the second wire rod part. Therefore, the present nasal cavity insertion device fixture can reduce an area making contact with the bottom end of the bridge of the nose. Consequently, the present nasal cavity insertion device fixture can relieve a strange feeling with respect to the bridge of the nose of a patient of sleep disorder.

A nasal cavity insertion device fixture according to a fourteenth aspect of the present invention relates to the nasal cavity insertion device fixture according to any one of the ninth to thirteenth aspects, and wherein a folded-back section between the first wire rod part and the second wire rod part has a linear shape.

Therefore, the present nasal cavity insertion device fixture does not stand out at the bottom end of the bridge of the nose of a patient of sleep disorder. Therefore, the present nasal cavity insertion device fixture can make a patient of sleep disorder no different in appearance from usualness.

A nasal cavity insertion device fixture according to a fifteenth aspect of the present invention relates to the nasal cavity insertion device fixture according to any one of the ninth to fourteenth aspects. The present nasal cavity insertion device fixture further includes a circular wire rod part. The circular wire rod part is formed on a conceptual plane arranged roughly perpendicularly to an axis of the first wire rod part on an opposite side of a second wire rod part formed side of the first wire rod part.

Therefore, the present nasal cavity insertion device fixture can fit the circular wire rod part to the inside of a nasal passage. Thus, the present nasal cavity insertion device fixture can firmly fix the device not only to the bridge of the nose but also to either of the nasal passages. Consequently, the present nasal cavity insertion device fixture can fix the device in a further better condition.

A nasal cavity insertion device fixture according to a sixteenth aspect of the present invention relates to the nasal cavity insertion device fixture according to any one of the ninth to fifteenth aspects, and wherein the second wire rod part is provided with a length adjusting portion adjusting a length of the second wire rod part.

Therefore, the tip of the device can be disposed at a desired position in the pharynx by adjusting the length of the second wire rod part in accordance with the length from a nasal passage to the pharynx of a patient.

A nasal cavity insertion device fixture according to a seventeenth aspect of the present invention relates to the nasal cavity insertion device fixture according to any one of the ninth to sixteenth aspects. The present nasal cavity insertion device fixture further includes a resinous coating coating the wire rod.

Therefore, occurrence of metal allergy attributed to a metal wire rod can be inhibited.

A nasal cavity insertion device set according to an eighteenth aspect of the present invention includes the nasal cavity insertion device fixture according to any one of the first to seventeenth aspects and a device to be inserted into a nasal cavity.

A nasal cavity insertion device set according to a nineteenth aspect of the present invention relates to the nasal cavity insertion device set according to the eighteenth aspect, and wherein the device has a plurality of holes or thin portions disposed at predetermined intervals as attachment positions for the nasal cavity insertion device fixture.

According to the aforementioned configuration, the position of the nasal cavity insertion device fixture can be adjusted in accordance with the length from a nasal passage to the pharynx of a patient by appropriately selecting any one of the holes or the thin portions as the attachment positions on an as-needed basis. Therefore, the tip of the device can be disposed at a desired position in the pharynx.

A nasal cavity insertion device set according to a twentieth aspect of the present invention relates to the nasal cavity insertion device set according to the eighteenth aspect or the nineteenth aspect, and wherein the device includes a flange on a base end portion thereof.

According to the aforementioned configuration, the flange on the base end section of the device makes contact with the sidewall of a nasal passage, and thereby, the device can be prevented from dropping to the direction of the pharynx.

A nasal cavity insertion device set according to a twenty-first aspect of the present invention relates to the nasal cavity insertion device set according to the eighteenth aspect or the nineteenth aspect, and wherein a base end section of the device has a tapered shape with a diameter increased towards an end thereof.

According to the aforementioned configuration, the device can be prevented from dropping to the direction of the pharynx by setting the outer diameter of the base end section of the device to be greater than the diameter of a nasal passage.

A nasal cavity insertion device set according to a twenty-second aspect of the present invention relates to the nasal cavity insertion device set according to the twenty-first aspect, and wherein the tapered base end section has a single or plurality of through holes.

According to the aforementioned configuration, air permeability between the inside and the outside of a nasal passage can be reliably achieved through the through hole/holes by forming the base end section of the device in a tapered shape even when the base end section is disposed while covering a nasal passage.

DESCRIPTION OF THE EMBODIMENTS

—First Embodiment—

Figure 1:
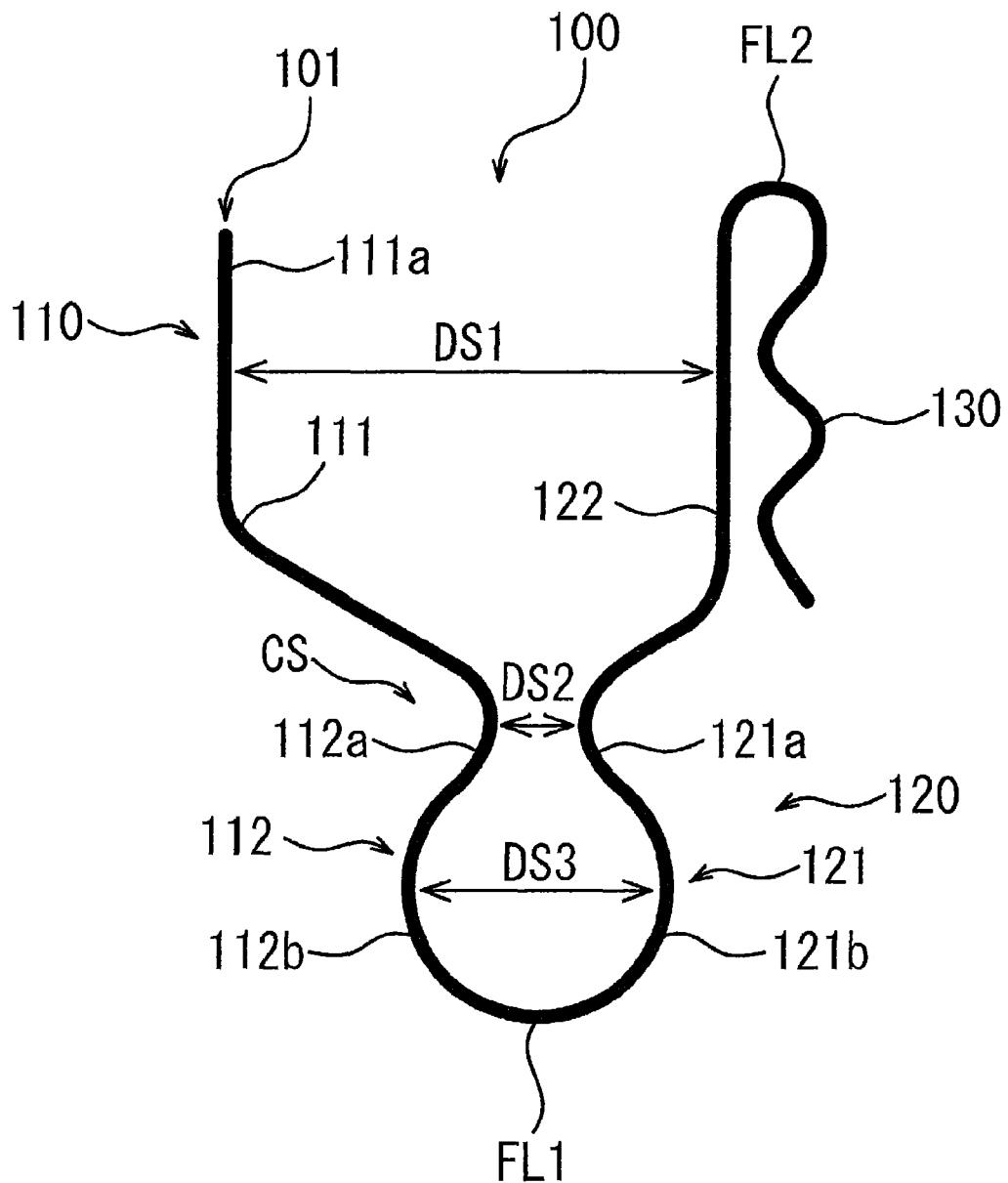
FIG. 1 is a front view of a nasal cavity insertion tube fixture according to a first embodiment of the present invention.

A nasal cavity insertion tube fixture (hereinafter simply referred to as a fixture on an as-needed basis) 100 according to a first embodiment of the present invention is a fixture for fixing a nasal cavity insertion tube 200 (see FIG. 2) to a bridge of the nose NP (see FIG. 3) and is formed with a wire rod 101 as shown in FIG. 1.

Figure 2:
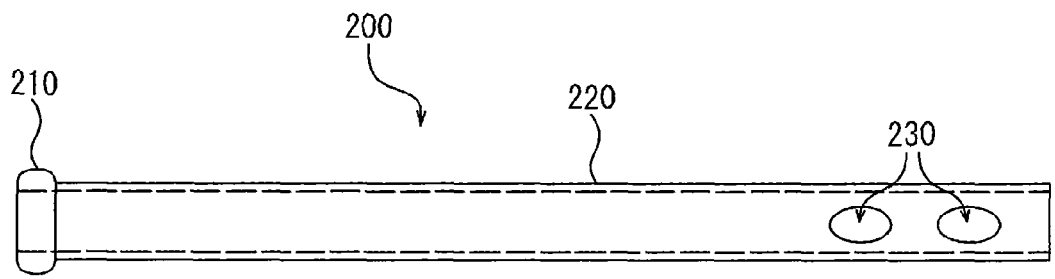
FIG. 2 is a schematic diagram showing an example of a nasal cavity insertion tube to which the nasal cavity insertion tube fixture according to the first embodiment of the present invention is connected.

It should be noted in the present embodiment that the nasal cavity insertion tube 200 is formed with a main body part 220, a tip portion 210 and openings 230 as shown in FIG. 2. The main body part 220 is a tubular body made of silicone resin. As shown in FIG. 2, the tip portion 210 has a ring shape and is disposed on a tip of the main body part 220. Two openings 230 are formed in the base end side section of the main body part 220 while penetrating through the sidewall of the main body part 220.

For easy explanation of the fixture 100, the wire rod 101 is hereinafter assumed to be formed by mainly three parts, i.e., a first wire rod part 110, a second wire rod part 120 and a third wire rod part 130 (see FIG. 1).

<Configuration of Fixture>

(1) First Wire Rod Part

As shown in FIG. 1, the first wire rod part 110 is mainly formed by an angle bracket shaped ("<" shaped) section 111 and an inverted S-shaped section 112.

(2) Second Wire Rod Part

As shown in FIG. 1, the second wire rod part 120 is continued to the first wire rod part 110, and is formed to be opposed to the first wire rod part 110 by folding back the wire rod 101 at a first folded-back portion FL1. Further, as shown in FIG. 1, it could be also mentioned that the second wire rod part 120 is mainly formed by an S-shaped section 121 and a linear section 122.

It should be noted in the present embodiment that the linear section 122 is opposed to the "<" shaped section 111 of the first wire rod part 110, while the S-shaped section 121 is opposed to the inverted S-shaped section 112 of the first wire rod part 110. Further, as shown in FIG. 1, the linear section 122 is separated at a first distance DS1 away from an upper portion 111a of the "<" shaped section 111 of the first wire rod part 110. Further, an upper portion 121a of the S-shaped section 121 is separated at a second distance DS2 away from an upper portion 112a of the inverted S-shaped section 112 of the first wire rod part 110. Further, a lower portion 121b of the S-shaped section 121 is separated at a third distance DS3 away from a lower portion 112b of the inverted S-shaped section 112 of the first wire rod part 110. Further, the second distance DS2 is set to be less than the first distance DS1 and the third distance DS3. As a result, a constricted section CS is formed in the fixture 100. Further, the constricted section CS functions as a clip with respect to the bridge of the nose NP (see FIG. 3) in the present embodiment (see FIG. 3).

(3) Third Wire Rod Part

As shown in FIG. 1, the third wire rod part 130 is continued to the second wire rod part 120, and is formed to be opposed to the second wire rod part 120 on the opposite side of the first wire rod part formed side of the second wire rod part 120 by folding back the wire rod 101 at a second folded-back portion FL2 in a direction opposite to the second wire rod part 120. Further, this third wire rod part 130 has a wavy shape as shown in FIG. 1. Moreover, in the present embodiment, the third wire rod part 130 functions as a clip for the sidewall of the nasal cavity insertion tube 200 together with the linear section 122 of the second wire rod part 120 (see FIG. 3).

<Method of Using Fixture>

Figure 3:
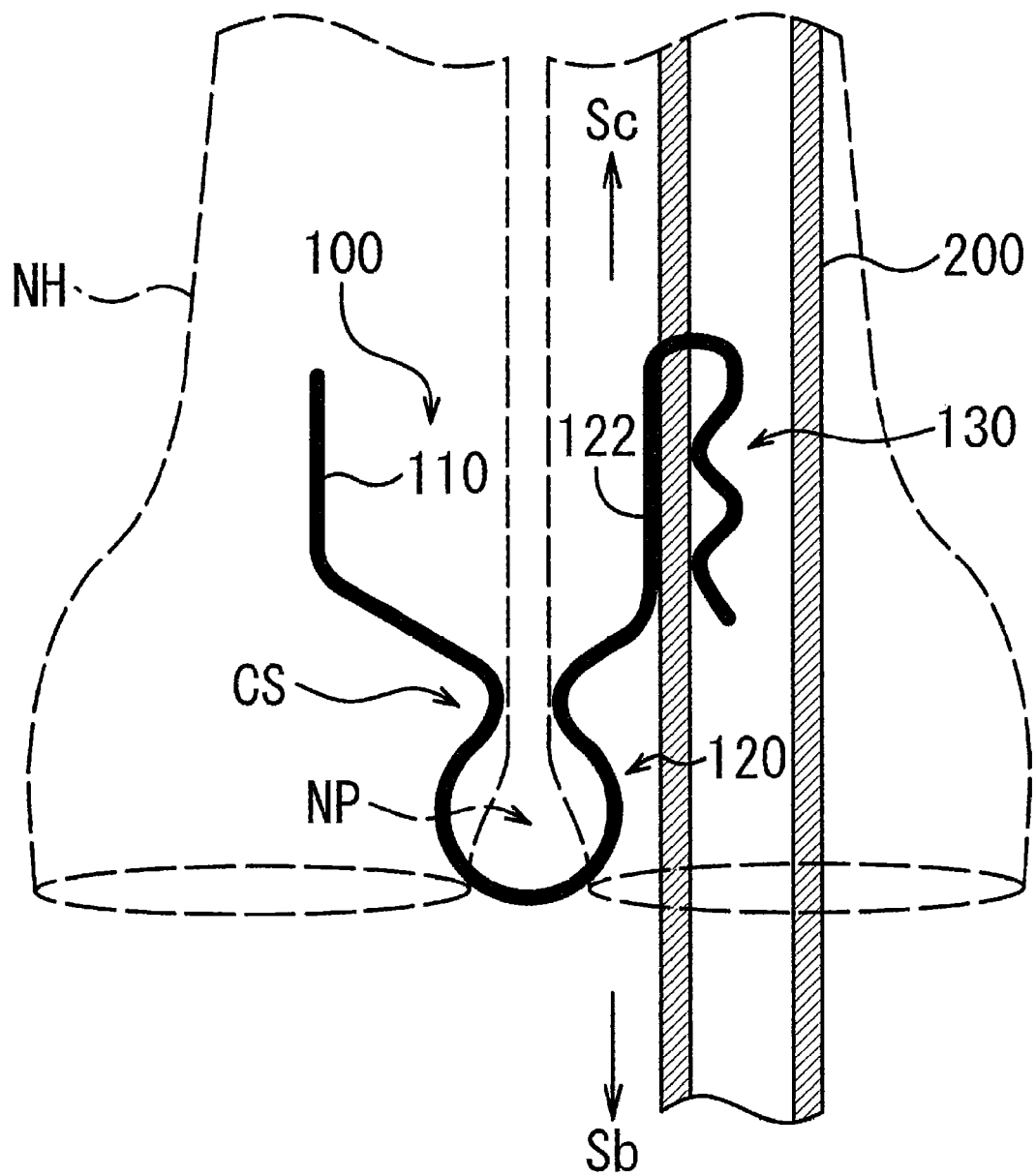
FIG. 3 is a schematic diagram showing a state that the nasal cavity insertion tube is fixed to the bridge of the nose using the nasal cavity insertion tube fixture according to the first embodiment of the present invention.

First, as shown in FIG. 3, the tip portion of the third wire rod part 130 is pierced through a base end side Sb sidewall of the nasal cavity insertion tube 200 and the sidewall is clipped between the third wire rod part 130 and the linear section 122 of the second wire rod part 120. Next, under the condition, the nasal cavity insertion tube 200 is inserted from a tip side Sc into either of nasal passages NH, and the tip portion 210 of the nasal cavity insertion tube 200 (see FIG. 2) is inserted toward the pharynx (See FIG. 3). Then, finally, the tip portion 210 of the nasal cavity insertion tube 200 (see FIG. 2) is inserted into the pharynx, and simultaneously, the bottom end portion of the bridge of the nose NP is clipped with the constricted section CS (see FIG. 3). It should be herein noted that the tip of the first wire rod part 110 exists in the nasal passage NH.

When being removed from the bridge of the nose NP, the fixture 100 may be pulled out while being simply held with a hand.

<Features of Fixture>

(1)

The fixture 100 according to the embodiment of the present invention includes the constricted section CS functioning as a clip for the bridge of the nose NP, the third wire rod part 130 and the linear section 122 of the second wire rod part 120, both of which function as a clip for the sidewall of the nasal cavity insertion tube 200. Therefore, this fixture 100 can firmly fix the nasal cavity insertion tube 200 to the bridge of the nose NP. Consequently, the fixture 100 can prevent displacement or detachment of the nasal cavity insertion tube 100 during the sleep of a patient of sleep disorder.

Further, a user of the fixture 100 wears the fixture 100 to one's nose existing within close reach. In other words, the user can wear the fixture 100 and the nasal cavity insertion tube 200 by oneself.

(2)

The fixture 100 according to the embodiment of the present invention employs the constricted section CS as a clip for the bridge of the nose NP. The fixture 100 can thereby reduce an area in a part thereof making contact with the bottom end portion of the bridge of the nose NP. Therefore, the fixture 100 can reduce the uncomfortable feeling of a patient of sleep disorder with respect to the bridge of the nose.

(3)

In the fixture 100 according to the embodiment of the present invention, the third wire rod part 130 is formed in a wavy shape. Therefore, when the sidewall of the nasal cavity insertion tube 200 is clipped between the third wire rod part 130 and the linear section 122 of the second wire rod part 120, the sidewall of the nasal cavity insertion tube 200 and the third wire rod part 130 can make contact with each other at less contact points. Therefore, a patient of sleep disorder can more easily perform an operation of clipping the sidewall of the nasal cavity insertion tube 200 between the third wire rod part 130 and a part of the second wire rod part 120.

<Variations>

(A)

Figure 4:
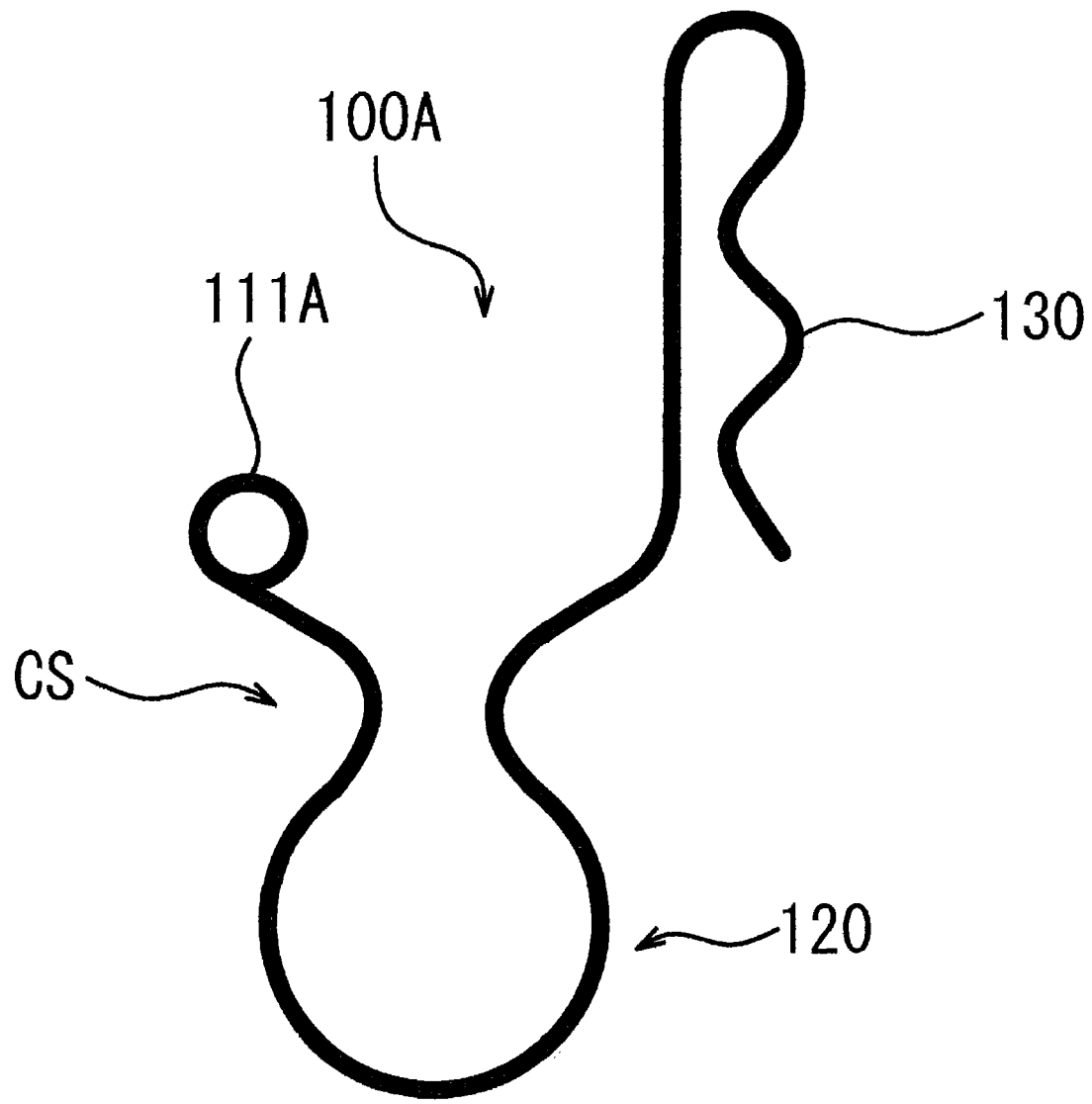
FIG. 4 is a front view of a nasal cavity insertion tube fixture according to a variation (A) of the first embodiment of the present invention.

In the aforementioned embodiment, the fixture 100 as shown in FIG. 1 has been introduced as an example. However, the present invention encompasses a fixture 100A as shown in FIG. 4.

Such a fixture 100A is the same as the fixture 100 according to the aforementioned embodiment except for that the "<" shaped section 111 of the first wire rod part 110 is substituted with a first circular wire rod part 111A. It should be noted that the first circular wire rod portion 111A is formed on the same plane as the second wire rod part 120 and the third wire rod part 130.

(B)

Figure 5:
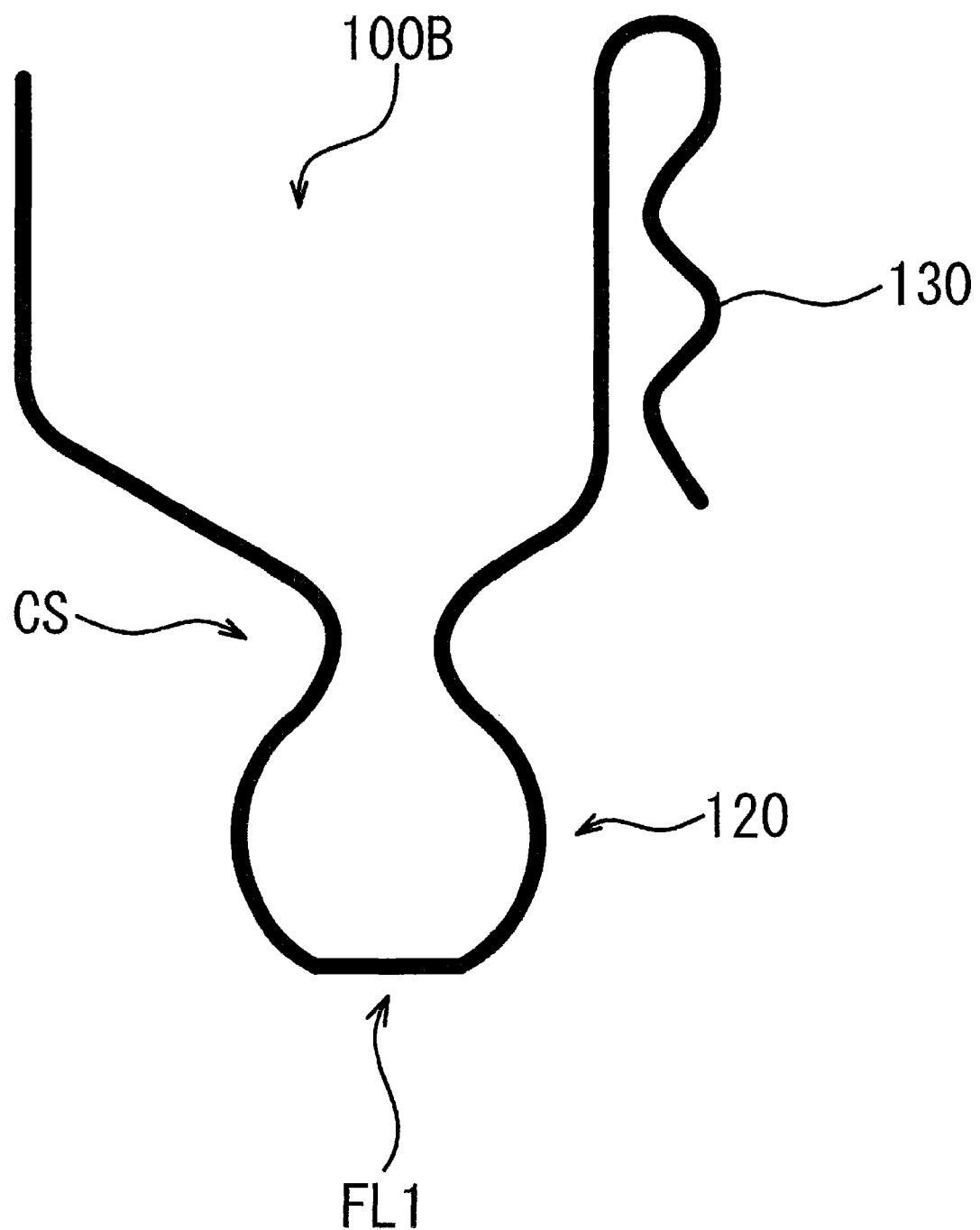
FIG. 5 is a front view of a nasal cavity insertion tube fixture according to a variation (B) of the first embodiment of the present invention.

In the aforementioned embodiment, the fixture 100 as shown in FIG. 1 has been introduced as an example. However, a fixture 100B as shown in FIG. 5 is also in the scope of the present invention.

Such a fixture 100B is the same as the fixture 100 according to the aforementioned embodiment except for that the shape of the first folded-back portion FL1 is changed from a circular-arc shape to a linear shape. With the configuration, the fixture 100B less stands out at the bottom end of the bridge of the nose NP of a patient of sleep disorder when being worn. Therefore, the fixture 100B can make a patient of sleep disorder no different in appearance from usualness.

(C)

Figure 6:
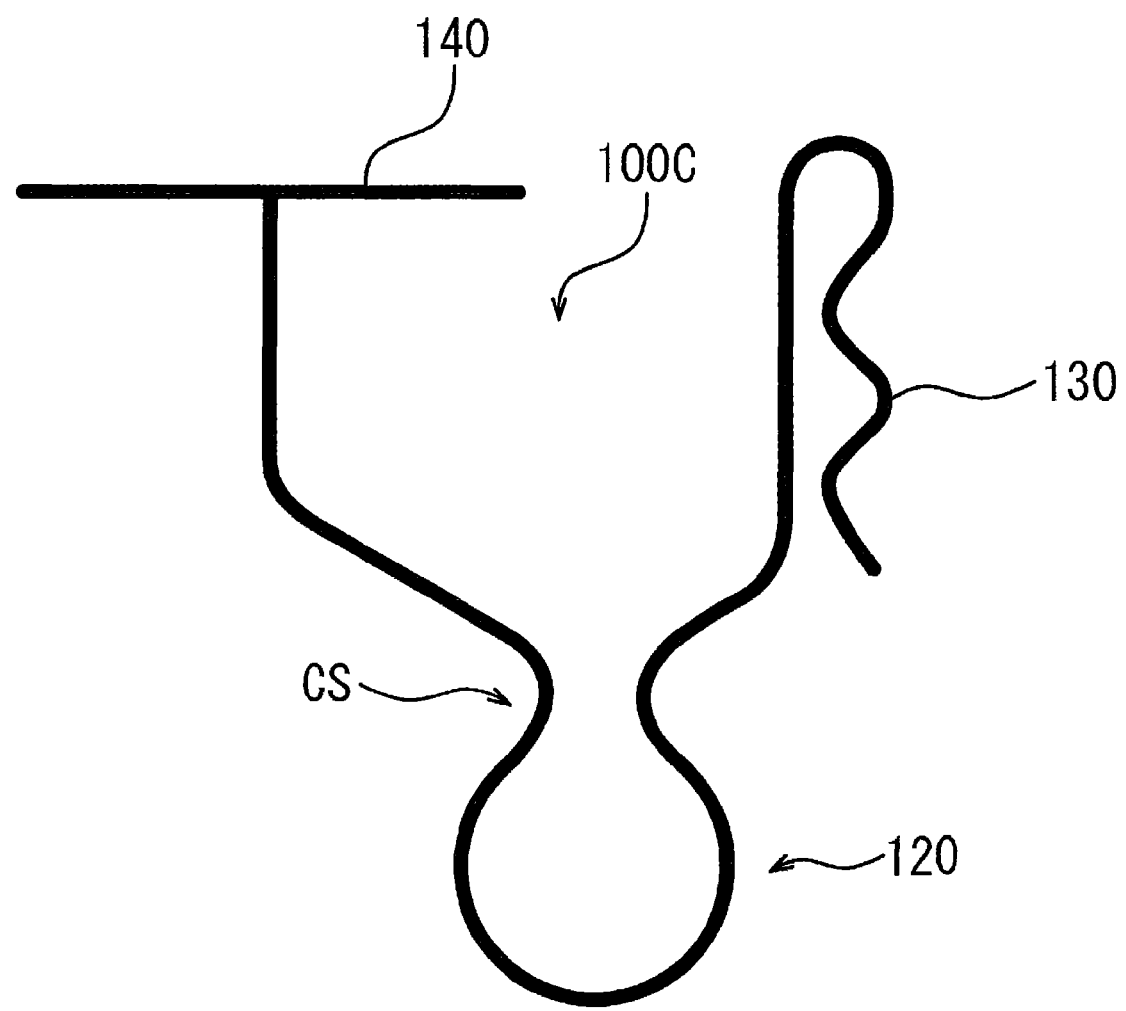
FIG. 6 is a front view of a nasal cavity insertion tube fixture according to a variation (C) of the first embodiment of the present invention.
Figure 7:
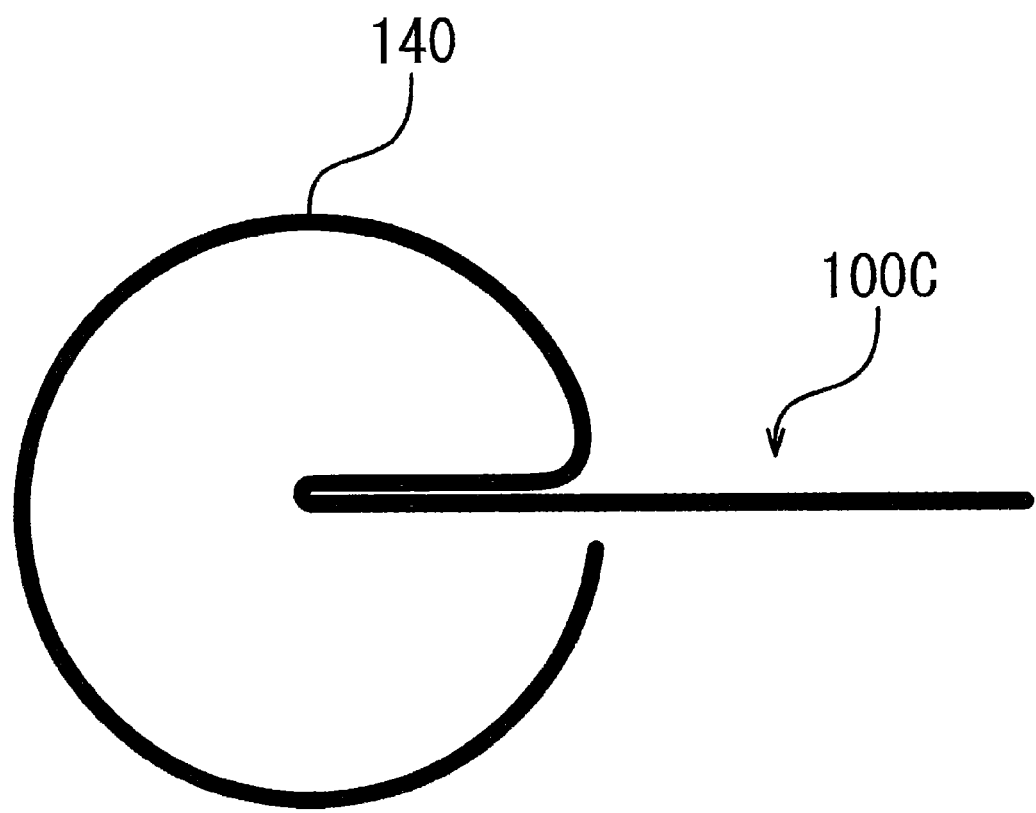
FIG. 7 is a plan view of the nasal cavity insertion tube fixture according to the variation (C) of the first embodiment of the present invention.

In the aforementioned embodiment, the fixture 100 as shown in FIG. 1 has been introduced as an example. However, a fixture 100C as shown in FIGS. 6 and 7 is also in the scope of the present invention.

Such a fixture 100C is the same as the fixture 100 according to the aforementioned embodiment except for that a second circular wire rod part 140 is formed anew on the tip of the first wire rod part 110. It should be noted that the second circular wire rod part 140 is formed along a conceptual plane arranged perpendicularly to the axis of the upper portion 111a of the "<" shaped section 111 of the first wire rod part 110.

Figure 8:
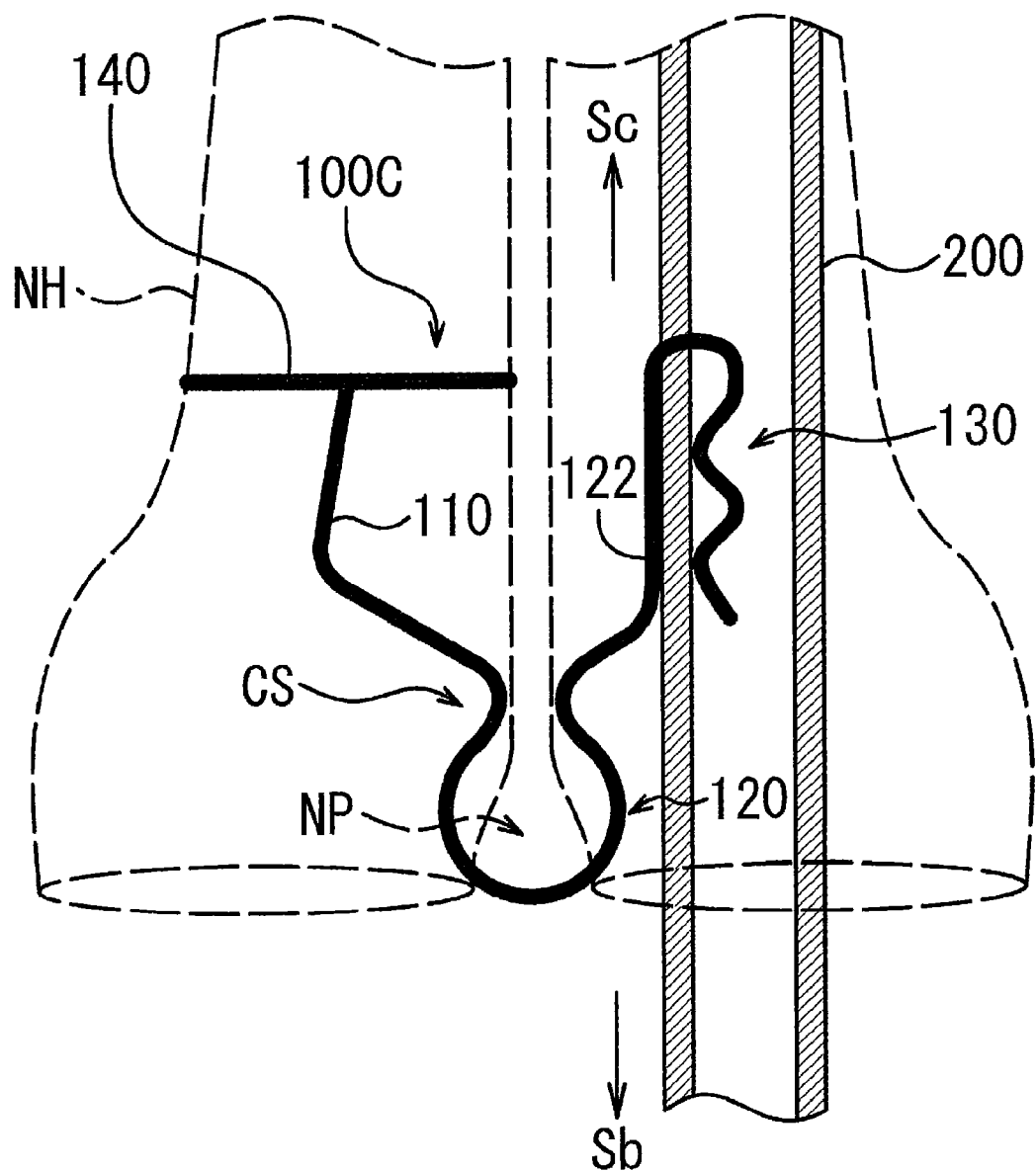
FIG. 8 is a schematic diagram showing a state that the nasal cavity insertion tube is fixed to the bridge of the nose and the nasal passages using the nasal cavity insertion tube fixture according to the variation (C) of the first embodiment of the present invention.

In such a fixture 100C, as shown in FIG. 8, the second circular wire rod part 140 can be fitted within one of the nasal passages NH. Therefore, such a fixture 100C can firmly fix the nasal cavity insertion tube 200 not only to the bridge of the nose NP but also to either of the nasal passages NH. Therefore, such a fixture 100C can fix the nasal cavity insertion tube 200 in a better condition.

(D)

In the fixture 100 according to the aforementioned embodiment, the second distance DS2 is set to be less than the third distance DS3. However, the second distance DS2 may be set to be roughly equal to the third distance DS3. In this case, a U-shape is formed by the combination of the inverted S-shaped section 112 of the first wire rod part 110 and the S-shaped section 121 of the second wire rod part 120.

(E)

Figure 11:
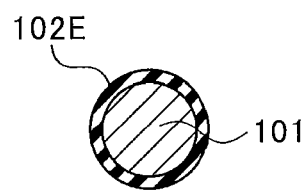
FIG. 11 is a cross-sectional view of a fixture according to a variation (E) of the first embodiment of the present invention.

Although not particularly described in the aforementioned embodiment, the wire rod 101 may be a round wire, a rectangular wire or a thin rectangular wire. Further, the material forming the wire rod is not particularly limited, but may be metal, resin and etc., for instance. When the wire rod is herein made of metal, a coating 102E made of resin (e.g., silicone rubber) may be provided for coating the wire rod 101 made of metal as shown in FIG. 11. Accordingly, metallic allergy attributed to the metal wire rod can be suppressed from being caused.

It should be noted that in the aforementioned variation (E), silicone rubber has been exemplified as a resin coating the wire rod 101 made of metal. However, the present invention is not limited to this, and the following reins can be applied other than silicone rubber as the coating 102E. Specific examples are: ABS resin (acrylonitrile-butadiene-styrene); butadiene-styrene rubber; polyester copolymer; ethylene-propylene rubber (ethylene-propylene-terpolymer rubber); EVA resin (ethylene-vinylacetate copolymer); high-density polyethylene; high-density polypropylene; impact-resistant polystyrene; low-density polyethylene; methyl-metacrylate-acrylonitrile-butadiene-styrene copolymer; chloroprene rubber; nitrilebutadiene rubber; polyamide resin; PETG resin; polyacetal resin; polybutyleneterephthalate resin; polycarbonate resin; polyethersulfone resin; polyethylene resin; polyethyleneterephthalate resin; polyimide resin; isobutylene-isoprene copolymer; polypropylene resin; polystyrene resin; polysulfone resin; polytetrafluoroethylene resin; polyurethane resin; polyvinylacetate resin; polyvinylchloride resin; styrene-butadiene resin; styrene-butadiene rubber; acrylic modified silicone resin; and one-component RTV (Room Temperature Vulcanizable) rubber.

(F)

Figure 12:
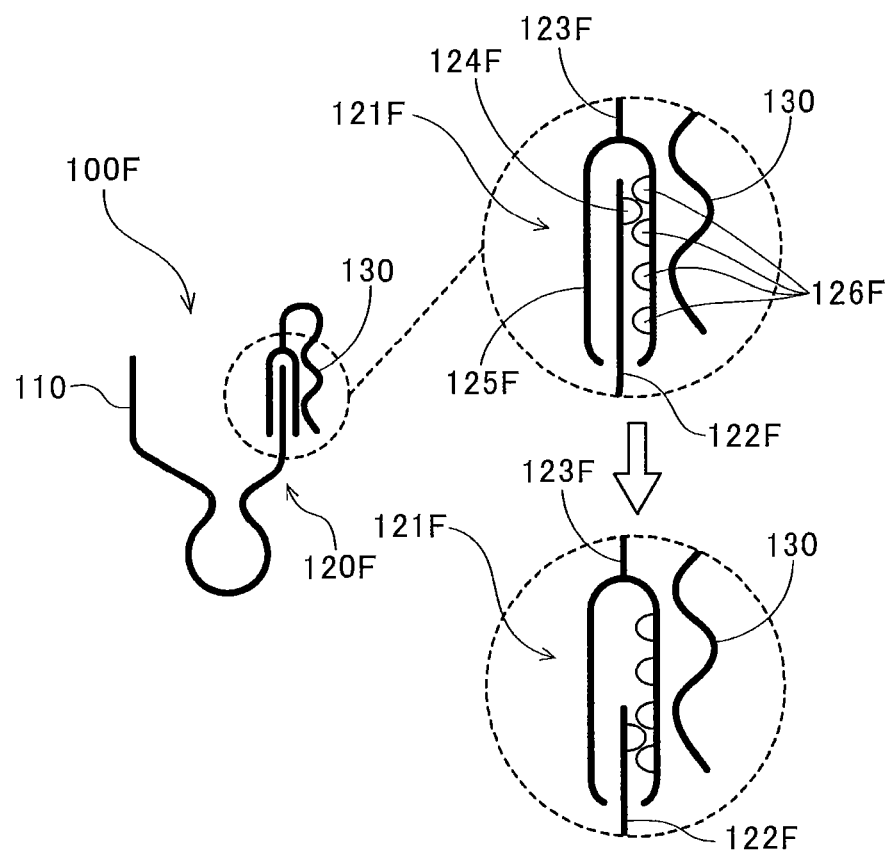
FIG. 12 includes a front view and a partial enlarged view of a fixture according to a variation (F) of the first embodiment of the present invention.

Further, in the aforementioned embodiment and the variations thereof, the fixtures 100, 100A, 100B and 100C have been introduced, each of which is formed by bending a single continuous wire rid. However, a fixture 100F having a length adjusting function as shown in FIG. 12 is also in the scope of the present invention.

Such a fixture 100F is the same as the fixture 100 according to the aforementioned embodiment except for that a second wire rod part 120F is provided with an adjusting portion 121F configured to adjust the length of the second wire rod part 120F. It should be herein noted that the other elements excluding the adjusting portion 121F will not be explained. In the fixture 100F according to the present variation, the second wire rod part 120F is divided into a section 122F continued to the first wire rod part 110 and a section 123F continued to the third wire rod part 130. Further, a convex portion 124F is attached to the tip of the section 122F continued to this first wire rod part 110. On the other hand, a hollow-shaped tube body 125F is attached to the tip of the section 123F continued to this third wire rod part 130 in order to enclose the section 122F continued to the first wire rod part 110. Multiple convex portions 126F are provided at predetermined intervals within the tube body 125F. The length of the second wire rod part 120F is configured to be adjusted by fitting the convex portion 124F into any of the dent sections formed among the convex portions 126F. In other words, the adjusting portion 121F includes the section 122F continued to the first wire rod part 110, the section 123F continued to the third wire rod part 130, the convex portion 124F, the tube body 125F and the multiple convex portions 126F. It should be noted that the bottom end of the tube body 125F has an inwardly reduced diameter and functions as a retainer of the section 122F continued to the first wire rod part 110.

Accordingly, the tip of the nasal cavity insertion tube 200 can be disposed at a desired position in the pharynx by adjusting the length of the second wire rod part 120F in accordance with the length from the nasal passage to the pharynx of a patient.

(G)

Figure 13:
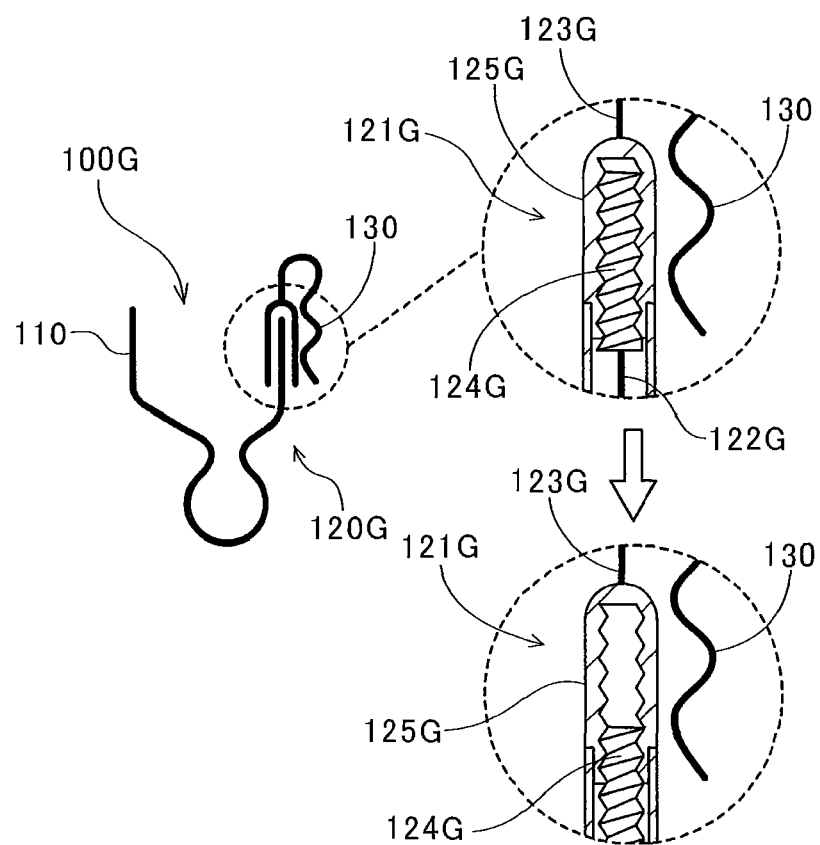
FIG. 13 includes a front view and a partial enlarged view of a fixture according to a variation (G) of the first embodiment of the present invention.

Further, except for the aforementioned fixture 100F having a length adjusting function, a fixture 100G having a length adjusting function as shown in FIG. 13 is also in the scope of the present invention.

Such fixture 100G is the same as the fixture 100 according to the aforementioned embodiment except for that a second wire rod part 120G is provided with an adjusting portion 121G configured to adjust the length of the second wire rod part 120G. It should be herein noted that the other elements excluding the adjusting portion 121G will not be explained. In the fixture 100G according to the present variation, the second wire rod part 120G is divided into a section 122G continued to the first wire rod part 110 and a section 123G continued to the third wire rod part 130. Further, a male-threaded shaft portion 124G is disposed on the tip of the section 122G continued to the first wire rod part 110. On the other hand, a tube body 125G, the inside of which is female-threaded, is attached to the tip of the section 123G continued to the third wire rod part 130. The length of the second wire rod part 120G is configured to be adjusted by screwing the male thread of the shaft portion 124G into the female thread of the tube body 125G. In other words, the adjusting portion 121G includes the section 122G continued to the first wire rod part 110, the section 123G continued to the third wire rod part 130, the shaft portion 124G and the tube body 125G. It should be noted that although not shown in the figures, similarly to the aforementioned tube body 125F, the bottom end of the tube body 125G also has an inwardly reduced diameter and functions as a retainer of the section 122G continued to the first wire rod part 110.

Accordingly, the tip of the nasal cavity insertion tube 200 can be disposed at a desired position in the pharynx by adjusting the length of the second wire rod part 120G in accordance with the length from the nasal passage to the pharynx of a patient.

(H)

Figure 15:
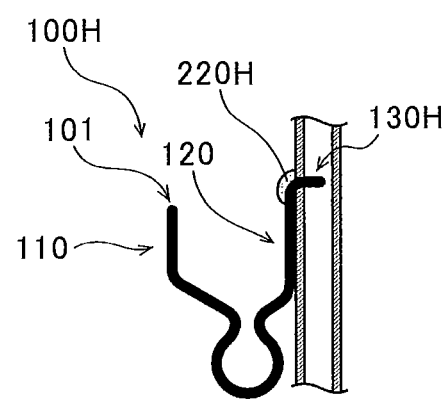
FIG. 15 is a front view showing a state that a fixture according to a variation (H) of the first embodiment of the present invention is attached to a nasal cavity insertion device.

In the aforementioned embodiment, the fixture 100 as shown in FIG. 1 has been introduced as an example. However, a fixture 100H as shown in FIG. 15 is also in the scope of the present invention.

Such a fixture 100H is the same as the fixture 100 according to the aforementioned embodiment except for that the third wire rod part 130, opposed to the second wire rod part 120 by folding back the wire rod 101, is substituted with a third wire rod part 130H extended oppositely to the first wire rod part 110 formed side. In other words, the fixture 100H according to the present variation is a fixture formed by the wire rod 101 and has the first wire rod part 110, the second wire rod part 120 and the third wire rod part 130H. Further, the third wire rod part 130H is continued to the second wire rod part 120, and is formed to be extended oppositely to the first wire rod part 110 formed side of the second wire rod part 120 by bending the wire rod 101.

As to a method of using the fixture 100H, the tip portion of the third wire rod part 130H is firstly pierced into the base end side sidewall of the nasal cavity insertion tube 200. Next, the outer peripheral surface of the nasal cavity insertion tube 200 and the second wire rod part 120 making contact with the outer peripheral surface are adhered by means of an adhesive 220H. Under the condition, the nasal cavity insertion tube 200 is inserted from its tip side into a nasal passage and the tip portion of the nasal cavity insertion tube 200 is gradually inserted toward the pharynx. Then, finally, the tip portion of the nasal cavity insertion tube 200 is inserted into the pharynx while the bottom part of the bridge of the nose is clipped with a part of the second wire rod part 120 and the first wire rod part 110. It should be noted that any of the materials exemplified in the variation (B) of the second exemplary embodiment to be described can be applied as the material of the adhesive 220H.

Figure 16:
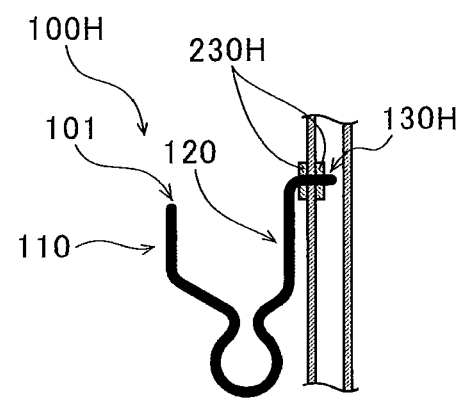
FIG. 16 is a front view of a condition that the fixture according to the variation (H) of the first embodiment of the present invention is attached to the nasal cavity insertion device by means of a fixing member.

In the fixture 100H according to the aforementioned variation (H), the example has been explained that the fixture 100H and the nasal cavity insertion tube 200 are adhered by means of the adhesive 220H. However, the present invention is not limited to the configuration, and as shown in FIG. 16, the fixture 100H and the nasal cavity insertion tube 200 may be fixed by means of a fixing member 230H. This fixing member 230H is formed by a pair of members disposed inside and outside the nasal cavity insertion tube 200. The fixing member 230H is attached to the third wire rod part 130H pierced into the sidewall of the nasal cavity insertion tube 200. Accordingly, the sidewall of the nasal cavity insertion tube 200 is clipped with the fixing member 230H, and the nasal cavity insertion tube 200 and the fixture 100H are thereby fixed.

(I)

Figure 17:
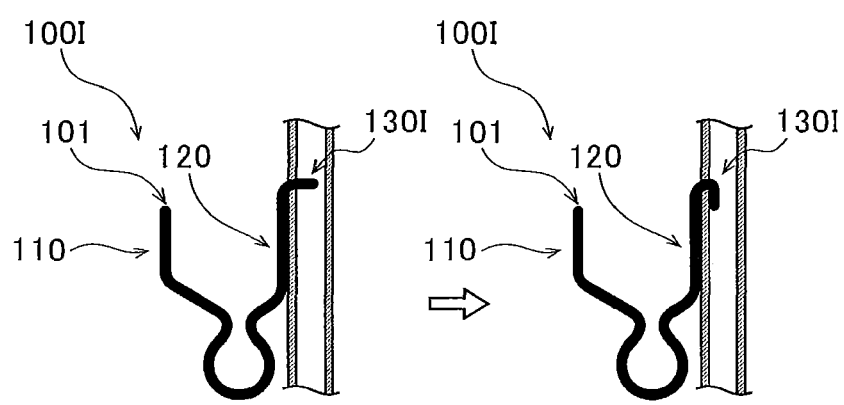
FIG. 17 is a front view showing a state that a fixture according to a variation (I) of the first embodiment of the present invention is attached to a nasal cavity insertion device.

In the aforementioned variation (H), the fixture 100H as shown in FIGS. 15 and 16 has been introduced as an example. However, a fixture 100I as shown in FIG. 17 is also in the scope of the present invention.

Such a fixture 100I is the same as the fixture 100H according to the aforementioned variation (H) except for that the third wire rod part 130 is structured to be bendable.

In other words, the fixture 100I according to the present variation is a fixture formed by the wire rod 101 and has the first wire rod part 110, the second wire rod part 120 and a third wire rod part 130I. Further, the third wire rod part 130I is continued to the second wire rod part 120, and is formed to be extended oppositely to the first wire rod part 110 formed side of the second wire rod part 120 by bending the wire rod 101. Yet further, the third wire rod part 130I is structured to be bendable. Accordingly, the third wire rod part 130I is prevented from coming off the nasal cavity insertion tube 200 while being bent within the nasal cavity insertion tube 200.

As to a method of using the fixture 100I, the tip portion of the third wire rod part 130I is firstly pierced into the base end side sidewall of the nasal cavity insertion tube 200. Next, the third wire rod part 130I is bent within the nasal cavity insertion tube 200. It is herein preferable to fix the fixture 100I and the nasal cavity insertion tube 200 by clipping the sidewall of the nasal cavity insertion tube 200 with the bent third wire rod part 130I and the second wire rod part 120. Under the condition, the nasal cavity insertion tube 200 is inserted from its tip side into a nasal passage, and the tip portion of the nasal cavity insertion tube 200 is gradually inserted toward the pharynx. Then, finally, the tip portion of the nasal cavity insertion tube 200 is inserted into the pharynx, while the bottom end of the bridge of the nose is clipped with a part of the second wire rod part 120 and the first wire rod part 110.

—Second Embodiment—

Figure 9:
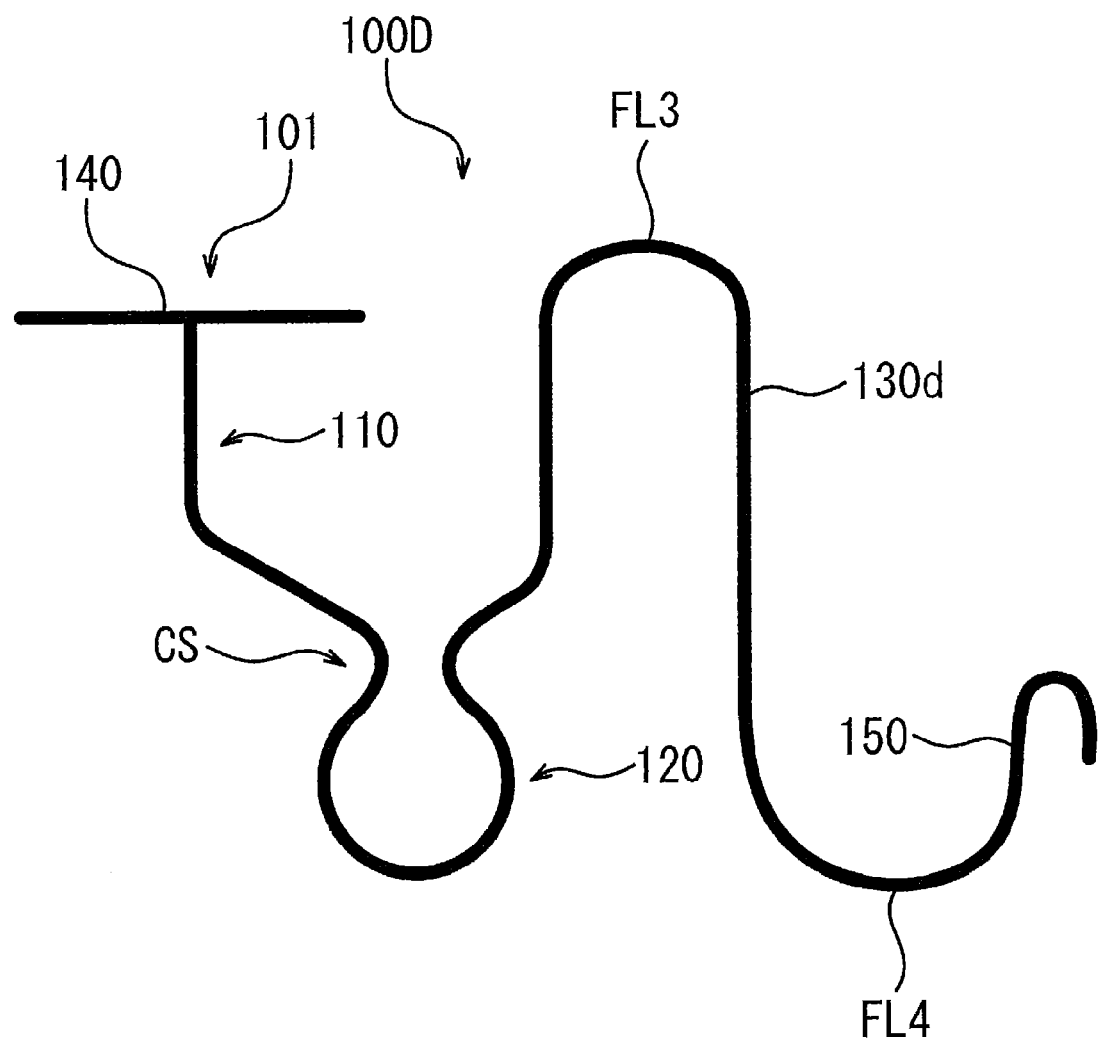
FIG. 9 is a front view of a nasal cavity insertion tube fixture according to a second embodiment of the present invention.

Similarly to the fixture 100 according to the first embodiment, a fixture 100D according to a second embodiment of the present invention is formed by the wire rod 101. Further, as shown in FIG. 9, the fixture 100D is mainly formed by the first wire rod part 110, the second wire rod part 120, a third wire rod part 130d, a fourth wire rod part 150 and the second circular wire rod part 140.

<Configuration of Fixture>

The first wire rod part 110 and the second wire rod part 120 are respectively the same as the first wire rod part 110 and the second wire rod part 120 according to the first embodiment. The second circular wire rod part 140 is the same as the second circular wire rod part 140 described in the variation (C) of the first embodiment.

The third wire rod part 130d and the fourth wire rod part 150, both of which do not exist in the fixtures 100, 100A, 100B and 100C according to the first embodiment and the variations thereof, will be hereinafter explained in detail.

(1) Third Wire Rod Part

Figure 10:
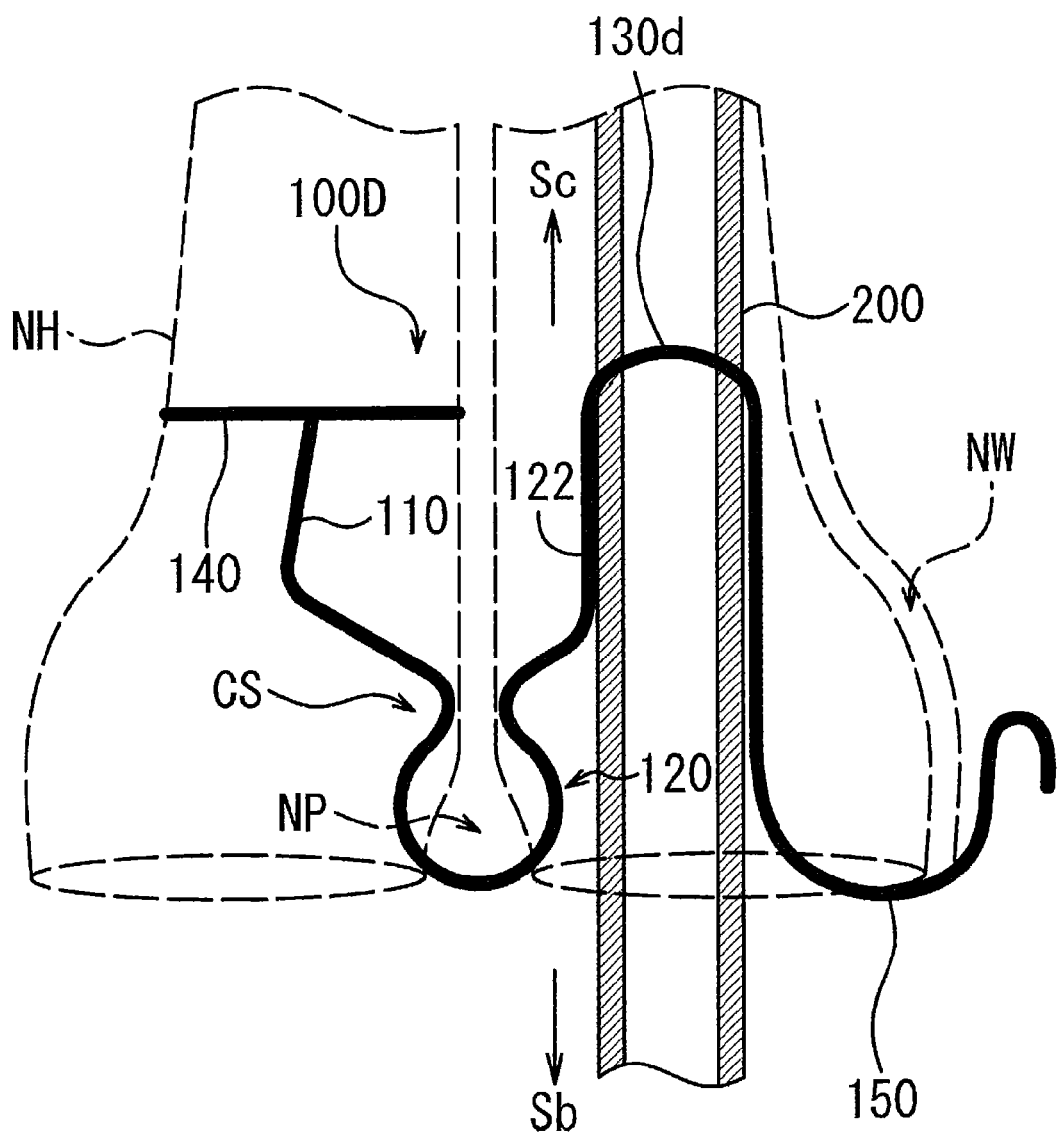
FIG. 10 is a schematic diagram showing a state that the nasal cavity insertion tube is fixed to the bridge of the nose and a nasal wing using the nasal cavity insertion tube fixture according to the second embodiment of the present invention.

As shown in FIG. 9, the third wire rod part 130d is continued to the second wire rod part 120, and is formed to be opposed to the second wire rod part 120 on the opposite side of the first wire rod formed side of the second wire rod part 120 by folding back the wire rod 101 oppositely to the second wire rod part 120 at a third folded-back portion FL3. Further, as shown in FIG. 10, the third folded-back portion FL3 serves to fix the nasal cavity insertion tube 200.

(2) Fourth Wire Rod Part

As shown in FIG. 9, the fourth wire rod part 150 is continued to the third wire rod part 130d, and is formed to be opposed to the third wire rod part 130d on the opposite side of the second wire rod formed side of the third wire rod part 130d by folding back the wire rod 101 oppositely to the third wire rod part 130d, i.e., in the same direction as the second wire rod part 120 at a fourth folded-back portion FL4. Further, as shown in FIG. 10, the fourth folded-back portion FL4 is disposed astride a nasal wing NW, and thus serves to prevent the nasal cavity insertion tube 200 from being inserted into a nasal passage NH and the patient's body more than necessity.

<Method of Using Fixture>

First, the tip portion of the fourth wire rod part 150 is pierced through the base end side Sb section of the nasal cavity insertion tube 200, and subsequently, the nasal cavity insertion tube 200 is moved to the third folded-back portion FL3. Next, under the condition, the nasal cavity insertion tube 200 is inserted from its tip side Sc into a nasal passage NH, and the tip portion 210 (see FIG. 2) of the nasal cavity insertion tube 200 is gradually inserted toward the pharynx. Then, finally, the tip portion 210 (see FIG. 2) of the nasal cavity insertion tube 200 is inserted into the pharynx, while the bottom end of the bridge of the nose NP is clipped with the constricted section CS. Thus, the fourth folded-back portion FL4 is herein positioned astride either of the nasal wings NW.

<Features of Fixture>

In the fixture 100D according to the embodiment of the present invention, the fourth folded-back portion FL4, exerting a burial prevention function for the nasal cavity insertion tube 200, is formed in addition to the constricted section CS functioning as a clip with respect to the bridge of the nose NP, the third wire rod part 130 and the linear section 122 of the second wire rod part 120, both of which function as a clip with respect to the sidewall of the nasal cavity insertion tube 200. Therefore, the fixture 100 can not only firmly fix the nasal cavity insertion tube 200 to the bridge of the nose NP but also prevent the nasal cavity insertion tube 200 from being inserted into a nasal passage NH and the body more than necessity during the sleep of a patient of sleep disorder. Therefore, the fixture 100 can prevent the displacement or the detachment of the nasal cavity insertion tube 100 during the sleep of a patient of sleep disorder.

<Variations>

The various variations of the first embodiment may be applied to the fixture 100D according to the aforementioned embodiment.

—Third Embodiment—

Figure 14:
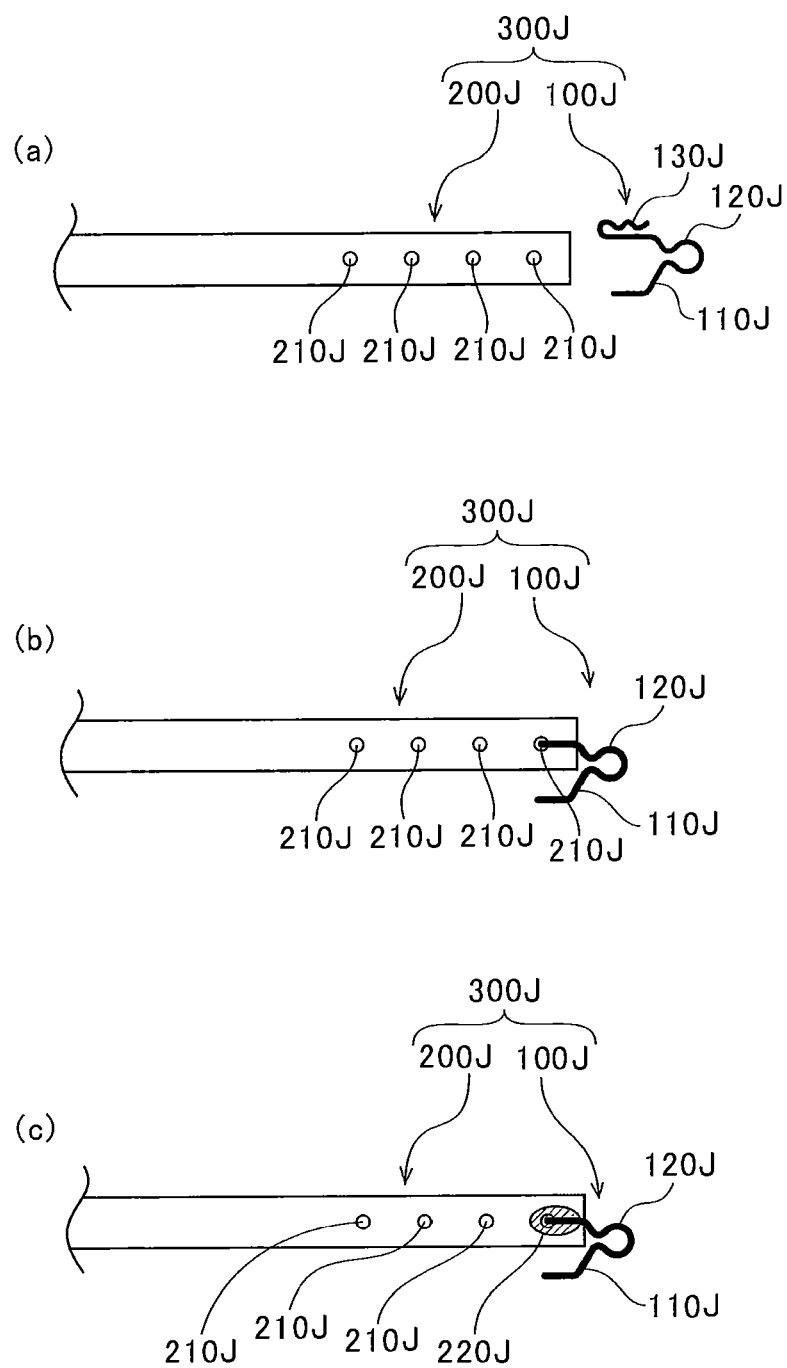
FIG. 14 includes schematic diagrams of a nasal cavity insertion device set according to a third embodiment of the present invention.

As shown in FIG. 14(*a*), a nasal cavity insertion device set 300J according to a third embodiment of the present invention includes a fixture 100J and a nasal cavity insertion tube 200J. It should be noted that the fixture 100J is similar to the fixture 100 according to the aforementioned first embodiment, and therefore, explanation thereof will be hereinafter omitted.

<Configuration of Tube>

The nasal cavity insertion tube 200J is a tube made of silicone rubber and has a length roughly the same as the distance from the entrance of a nasal passage to a pharynx. It should be noted that the fixture 100J can be attached to the base end side of the nasal cavity insertion tube 200J. Further, the nasal cavity insertion tube 200J has four thin portions 210J formed at predetermined intervals on the sidewall of the base end side section thereof. It should be herein noted that the example of forming the thin portions 210J has been explained. However, the present invention is not limited to the configuration, and the thin portions 210J may be holes penetrating through the sidewall. Further, the number of the thin portions 210J or the holes is not limited to four.

<Method of Using Nasal Cavity Insertion Device Set>

First, as shown in FIG. 14(*b*), the tip portion of a third wire rod part 130J is pierced into any one of the thin portions 210J formed on the base end side section of the nasal cavity insertion tube 200J. It is arbitrary selected which of the thin portions 210J should be pierced by the third wire rod part 130J depending on the length from a nasal passage to the pharynx of a patient. Then, the sidewall of the nasal cavity insertion tube 200J is clipped with the third wire rod part 130J and the linear section 122 of a second wire rod part 120J. Under the condition, as shown in FIG. 14(*c*), the second wire rod part 120J and the outer peripheral surface of the nasal cavity insertion tube 200J are adhered by means of an adhesive 220J (e.g., silicone rubber). Next, under the condition, the nasal cavity insertion tube 200J is inserted from the tip side Sc into either of the nasal passages NH, and the tip portion (not shown in the figure) of the nasal cavity insertion tube 200J is gradually inserted toward the pharynx. Then, finally, the tip portion (not shown in the figure) of the nasal cavity insertion tube 200J is inserted into the pharynx, while the bottom end of the bridge of the nose NP is clipped with the constricted section CS (see FIG. 3). It should be herein noted that the tip of a first wire rod part 110J exists in the nasal passage NH.

In detaching the fixture 100J from the bridge of the nose NP, the fixture 100J may be pulled out while being simply held with a hand.

<Features of Nasal Cavity Insertion Device Set>

In the nasal cavity insertion device set 300J according to the embodiment of the present invention, the fixture 100J is used, which is the same as the fixture 100 according to the first embodiment. Therefore, the fixture 100J has features similar to the features (1) to (3) of the fixture 100 according to the first embodiment and achieves advantageous effects similar to those achieved by the fixture 100 according to the first embodiment.

Further, the nasal cavity insertion tube 200J has the thin portions 210J formed at predetermined intervals on the lateral surface thereof. This makes it possible to adjust the position of the fixture 100J in accordance with the length from a nasal passage to a pharynx of a patient. Therefore, the tip of the nasal cavity insertion tube 200J can be disposed at a desired position in the pharynx.

<Variations>

(A)

The various variations of the first embodiment (100A, 100B, 100C, 100F, 100G, 100H and 100I, the fixture according to the second embodiment (100D) and the variations of the second embodiment may be applied to the fixture 100J of the nasal cavity insertion device set 300J according to the aforementioned embodiment.

(B)

In the nasal cavity insertion device set 300J according to the aforementioned embodiment, the example has been explained that the second wire rod part 120J and the outer peripheral surface of the nasal cavity insertion tube 200J are adhered by means of the adhesive 220J made of silicone rubber. However, the present invention is not limited to the configuration, and the following materials can be applied as the adhesive 220J other than the aforementioned silicone rubber. Specific examples are: allyltrichlorosilane; allyltriethoxysilane; allyltrimethoxysilane; diethoxymethylvinylsilane; trichlorovinylsilane; triethoxyvinylsilane; vinyltrimethoxysilane; 3-glycidyloxypropyl(dimethoxy) methylsilane; 3-glycidyloxypropyltrimethoxysilane; diethoxy(3-glycidyloxypropyl)methylsilane; 3-(2-aminoethylamino)propyldimethoxymethylsilane; 3-(2-aminoethylamino)propyltriethoxysilane; 3-(2-aminoethylamino)propyltrimethoxysilane; 3-aminopropyldiethoxymethylsilane; 3-aminopropyltriethoxysilane; 3-aminopropyltrimethoxysilane; (3-mercaptopropyl)triethoxysilane; (3-mercaptopropyl)trimethoxysilane; (chloromethyl) triethoxysilane; 1-[3-(trimethoxysilyl)propyl]urea; 2-(3,4-epoxycyclohexyl)

ethyltrimethoxysilane; 3-(triethoxysilyl)propyl isocyanate; 3-(triethoxysilyl)propyl methacrylate; 3-(trimethoxysilyl) propyl acrylate; 3-(trimethoxysilyl)propyl methacrylate; 3-chloropropyldimethoxymethylsilane; 3-chloropropyl-trichlorosilane; 3-chloropropyltriethoxysilane; 3-trimethoxysilylpropyl chloride; N-[2-(N-vinylbenzylamino)ethyl]-3-aminopropyltrimethoxysilane hydrochloride; trichloro(1H, 1H,2H,2H-tridecafluoro-n-octyl)silane; triethoxy-1H,1H, 2H,2H-tridecafluoro-n-octylsilane; trimethoxy(3,3,3-trifluoropropyl)silane; tetraethoxysilane; polyalkylsiloxane; polyalkylalkenylsiloxane; polyalkylhydrogensiloxane; acrylic modified silicone resin; and one-component RTV (Room Temperature Vulcanizable) rubber.

(C)

Figure 18:
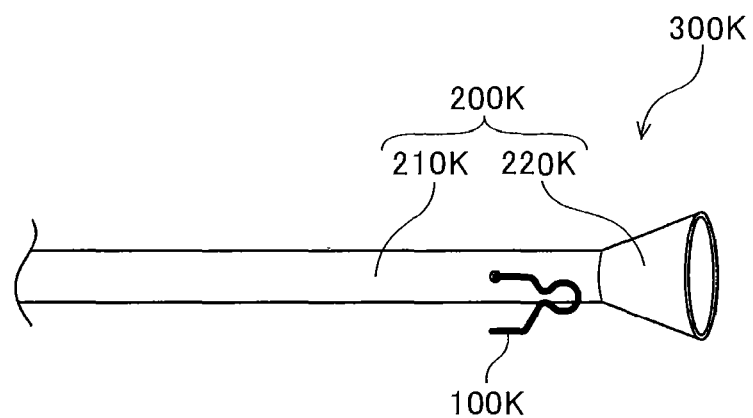
FIG. 18 is a schematic view of a nasal cavity insertion device set according to a variation (C) of the third embodiment of the present invention.

In the aforementioned embodiment, the nasal cavity insertion device set 300J as shown in FIG. 14 has been introduced as an example. However, a nasal cavity insertion device set 300K as shown in FIG. 18 is also in the scope of the present invention.

Such a nasal cavity insertion device set 300K is the same as the nasal cavity insertion device set 300J according to the aforementioned embodiment except for that a base end section 220K of a nasal cavity insertion tube 200K is tapered. In other words, as shown in FIG. 18, the nasal cavity insertion device set 300K according to the variation includes a fixture 100K and the nasal cavity insertion tube 200K. It should be noted that the fixture 100 according to the first embodiment, the various variations (100A, 100B, 100C, 100F, 100G, 100H and 100I) of the first embodiment, the fixture (100D) according to the second embodiment and the variation of the second embodiment may be applied to the fixture 100K.

Further, in the present embodiment, the nasal cavity insertion tube 200K includes a main body part 210K and the base end section 220K formed continuously to the main body part 210K. The base end section 220K is tapered so that the diameter thereof is gradually increased from the main body part 210K side to the end of the base end section 220K.

According to the aforementioned configuration, the nasal cavity insertion tube 200K can be prevented from dropping to the pharynx side by setting the outermost diameter of the base end section 220K of the nasal cavity insertion tube 200K to be greater than the diameter of a nasal passage.

(D)

Figure 19:
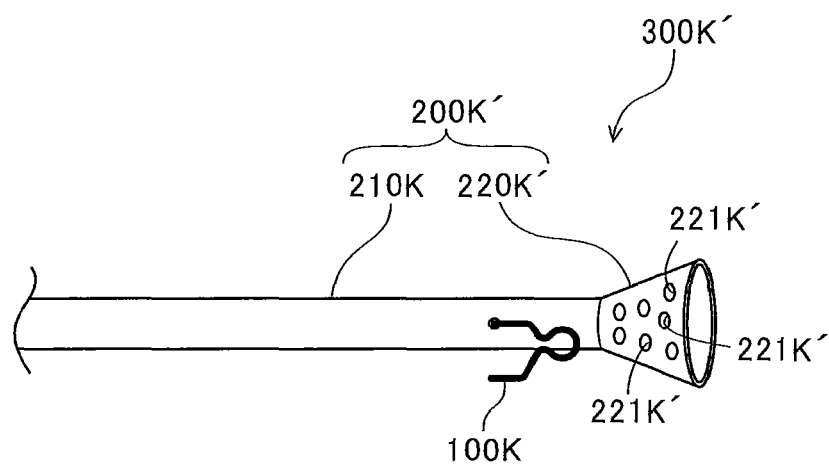
FIG. 19 is a schematic view of a nasal cavity insertion device set according to a variation (D) of the third embodiment of the present invention.

Further, in the aforementioned variation (C), the base end section 220K of the nasal cavity insertion tube 200K is tapered. In the present invention, however, a plurality of through holes 221K' may be formed in a tapered base end section 220K' of a nasal cavity insertion tube 200K' as with a nasal cavity insertion device set 300K' shown in FIG. 19. It should be noted that the present variation is similar to the aforementioned variation (C) except for that the through holes 221K' are formed in the base end section 220K' of the nasal cavity insertion tube 200K'. Therefore, the same reference numeral is assigned to an element similar to the corresponding one of the aforementioned variation (C) and explanation of the element will be hereinafter omitted.

According to the aforementioned configuration, the base end section 220K' of the tube 200K' is tapered, and thereby, air permeability between the inside and the outside of a nasal passage can be reliably achieved by the through holes 221K' even if the base end section 220K' is disposed while covering the nasal passage.

(E)

Figure 20:
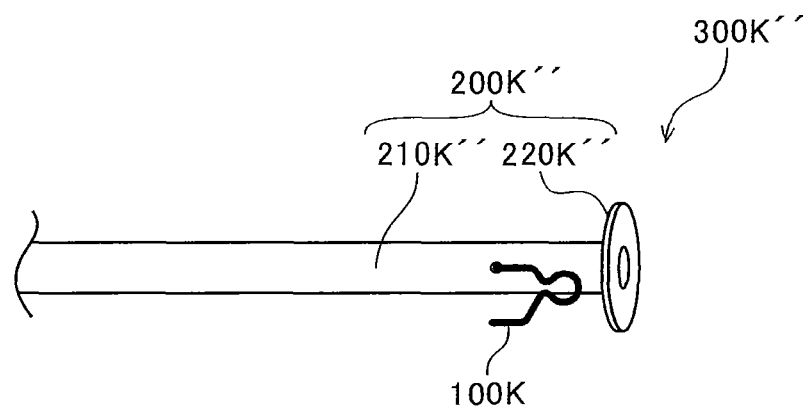
FIG. 20 is a schematic view of a nasal cavity insertion device set according to a variation (E) of the third embodiment of the present invention.

In the aforementioned embodiment, the nasal cavity insertion device set 300J as shown in FIG. 14 has been introduced as an example. However, a nasal cavity insertion device set 300K" as shown in FIG. 20 is also in the scope of the present invention.

Such a nasal cavity insertion device set 300K" is the same as the nasal cavity insertion device set 300J according to the aforementioned embodiment except for that a base end section 220K" of a nasal cavity insertion tube 200K" is flanged. In other words, as shown in FIG. 20, the nasal cavity insertion device set 300K" according to the present variation includes the fixture 100K and the nasal cavity insertion tube 200K". It should be noted that the fixture 100 according to the first embodiment, the various variations (100A, 100B, 100C, 100F, 100G, 100H and 100I) of the first embodiment, the fixture (100D) according to the second embodiment and the variation of the second embodiment may be applied to the fixture 100K.

Further, in the present embodiment, the nasal cavity insertion tube 200K" includes a main body part 210K" and the base end section 220K" formed continuously to the main body part 210K". The base end section 220K" is flanged.

According to the aforementioned configuration, the nasal cavity insertion tube 200K" can be prevented from dropping to the pharynx side by setting the outermost diameter of the base end section 220K" of the nasal cavity insertion tube 200K" to be greater than the diameter of a nasal passage.

—Fourth Embodiment—

Figure 21:
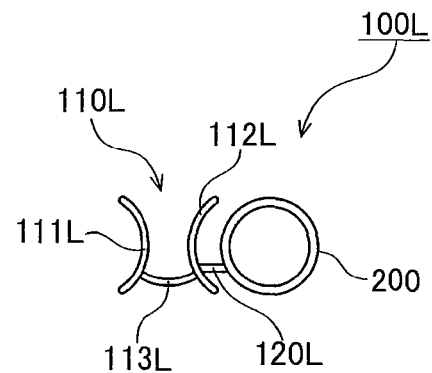
FIG. 21 is a front view of a fixture according to a fourth embodiment of the present invention.

As shown in FIG. 21, a fixture 100L according to a fourth embodiment of the present invention has a feature of fixing the nasal cavity insertion tube 200 to be inserted into a nasal cavity. Specifically, the fixture 100L includes a clip part 110L clipping the bridge of the nose and a connecting part 120L connecting the clip part 110L and the nasal cavity insertion tube 200. Further, the clip part 110L includes a first insertion portion 111L to be inserted into one of the nasal passages, a second insertion portion 112L to be inserted into the other of the nasal passages and a coupling portion 113L coupling the first insertion portion 111L and the second insertion portion 112L. The coupling portion 113L couples the first insertion portion 111L and the second insertion portion 112 so that the bridge of the nose can be pressed from its both sides by the first insertion portion 111L and the second insertion portion 112L. Further, the first insertion portion 111L and the second insertion portion 112L are both curved to be arranged along the inner peripheral surfaces of the nasal passages.

<Variations>

(A)

In the aforementioned embodiment, the fixture 100L as shown in FIG. 21 has been introduced as an example. However, a fixture 100L' as shown in FIG. 22 is also in the scope of the present invention.

Such a fixture 100L' is similar to the aforementioned fixture 100L except for that the fixture 100L' includes a hook portion 130L' to be hooked on a nasal wing. Therefore, explanation thereof will be hereinafter omitted. The hook portion 130L' is hooked on the nasal wing of a nasal passage different from the nasal passage to which the nasal cavity insertion tube 200 is inserted.

(B)

Figure 22:
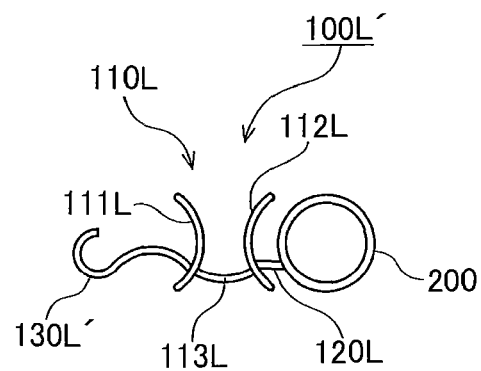
FIG. 22 is a front view of a nasal cavity insertion device set including a fixture according to a variation (A) of the fourth embodiment of the present invention.
Figure 23:
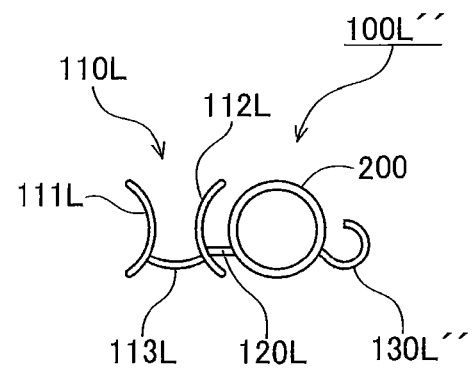
FIG. 23 is a front view of a nasal cavity insertion device set including a fixture according to a variation (B) of the fourth embodiment of the present invention.

In the aforementioned embodiment, the fixture 100L as shown in FIG. 22 has been introduced as an example. However, a fixture 100L" as shown in FIG. 23 is also in the scope of the present invention.

Such a fixture 100L" is similar to the aforementioned fixture 100L except for that the fixture 100L" includes a hook portion 130L" to be hooked on a nasal wing. Therefore, explanation thereof will be hereinafter omitted. Unlike the hook portion 130L' according to the aforementioned variation (A), the hook portion 130L" is hooked on the nasal wing of the nasal passage to which the nasal cavity insertion tube 200 is inserted.

As with the aforementioned variations (A) and (B), the nasal cavity insertion tube 200 can be fixed not only to the bridge of the nose but also to a nasal wing by providing the hook portion 130L', 130L" to be hooked on the nasal wing. Therefore, the displacement of the nasal cavity insertion tube 200 or the detachment of the device can be effectively prevented.

—Fifth Embodiment—

Figure 24:
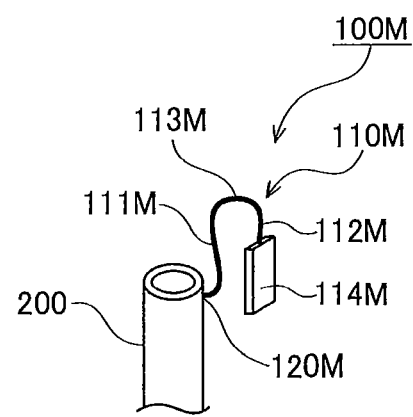
FIG. 24 is a front view of a fixture according to a fifth embodiment of the present invention.

As shown in FIG. 24, a nasal cavity insertion tube fixture 100M according to a fifth embodiment of the present invention has a feature of fixing the nasal cavity insertion tube 200 to be inserted into a nasal cavity. The nasal cavity insertion tube fixture 100M according to the fifth embodiment makes contact with the inside of a nasal passage for fixing the nasal cavity insertion tube 200. Specifically, the nasal cavity insertion tube fixture 100M includes a clip part 110M clipping the bridge of the nose and a connecting part 120M connecting the clip part 110M and the nasal civility insertion tube 200.

Further, the clip part 110M includes a first insertion portion 111M to be inserted into one nasal passage, a second insertion portion 112M to be inserted into the other nasal passage and a coupling portion 113M coupling the first insertion portion 111M and the second insertion portion 112M. Further, the first insertion portion 111M is a wire that the nasal cavity insertion tube 200 is connected to the tip thereof. Further, a plate-shaped member 114M is disposed on the tip of the second insertion portion 112M, while making surface contact with the inner peripheral surface of the other nasal passage.

<Variations>

(A)

Figure 25:
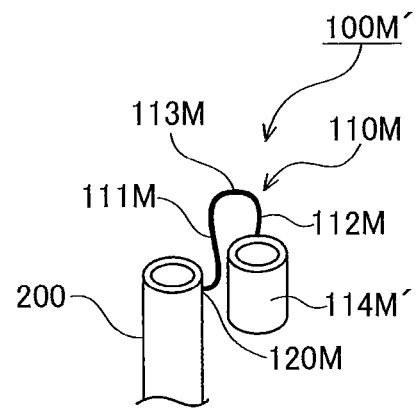
FIG. 25 is a perspective view of a nasal cavity insertion device set including a fixture according to a variation (A) of the fifth embodiment of the present invention.

In the aforementioned embodiment, the fixture 100M as shown in FIG. 24 has been introduced as an example . However, a fixture 100M' as shown in FIG. 25 is also in the scope of the present invention.

Such fixture 100M' is similar to the aforementioned fixture 100M except for that the second insertion portion 112M is provided with a tubular member 114M'. Therefore, explanation thereof will be hereinafter omitted. The tubular member 114M' is a flexibly deformable tube having an outer diameter greater than the average of the inner diameter of nasal passages. Further, the tubular member 114M' makes contact with the inner peripheral surface of the nasal passage. In the insertion into the nasal passage, the tubular member 114M' is inserted into the nasal passage while being reduced in its diameter. Accordingly, the tubular member 114M' is increased in its diameter in the inside of the nasal passage by means of the force of restoring to its original shape and makes contact with the inner peripheral surface of the nasal passage.

(B)

Figure 26:
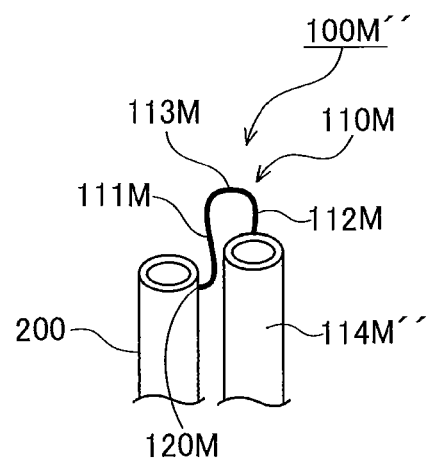
FIG. 26 is a perspective view of a nasal cavity insertion device set including a fixture according to a variation (B) of the fifth embodiment of the present invention.

In the aforementioned variation, the fixture 100M' including the tubular member 114M' has been introduced as an example. However, a fixture 100M" as shown in FIG. 26 is also in the scope of the present invention.

Such a fixture 100M" is similar to the aforementioned fixture 100M' except for that the second insertion portion 112M is provided with an elongated tubular member 114M". Therefore, explanation thereof will be hereinafter omitted. Similarly to the nasal cavity insertion tube 200, the elongated tubular member 114M" is extended from a nasal passage to a nasal cavity.

(C)

Figure 27:
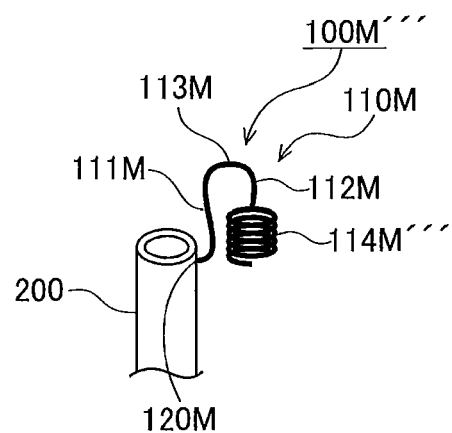
FIG. 27 is a perspective view of a nasal cavity insertion device set including a fixture according to a variation (C) of the fifth embodiment of the present invention.

In the aforementioned exemplary embodiment, the fixture 100M as shown in FIG. 24 has been introduced as an example. However, a fixture 100M''' as shown in FIG. 27 is also in the scope of the present invention.

Such a fixture 100M''' is similar to the aforementioned fixture 100M except for that the second insertion portion 112M is provided with a spring shaped member 114M'''. Therefore, explanation thereof will be hereinafter omitted. The spring shaped member 114M''' is a spring configured to be increased or reduced in its diameter depending on the inner diameter of a nasal passage. Further, the spring shaped member 114M''' makes contact with the inner peripheral surface of a nasal passage. When used, spring shaped member 114M''' can be thus inserted into a nasal cavity while being contracted even if the nasal cavity length is short. Therefore, the spring shaped member 114M''' is not required to be cut or the like in accordance with the nasal cavity length.

Each of the tubular member 114M' of the fixture 100M', the tubular shape member 114M" of the fixture 100M" and the spring shaped member 114M''' of the fixture 100M''' according to the aforementioned variations has an air permeable structure. Therefore, an air flow path can be reliably produced even when any of the members 114M', 114M" and 114M''' are disposed in a nasal passage. Thus, the members 114M', 114M" and 114M''' can be prevented from obstructing the breathing of a patient. In addition to this, a contact area with the fixture 114M', 114M", 114M''' is increased within the nasal passage. Therefore, pain of the bridge of the nose can be relieved.

—Sixth Embodiment—

Figure 28:
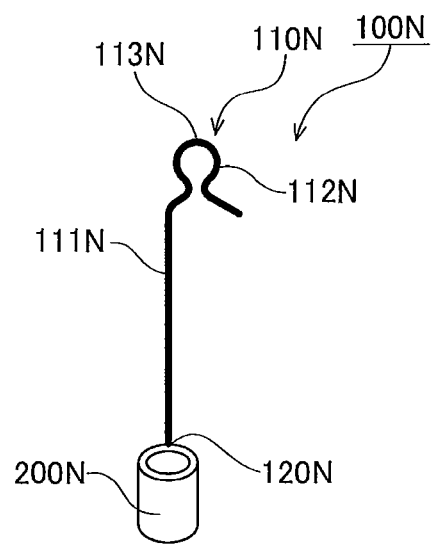
FIG. 28 is a perspective view of a nasal cavity insertion device set including a fixture according to a sixth embodiment of the present invention.

As shown in FIG. 28, a fixture N according to a sixth embodiment of the present invention has a feature of fixing the nasal cavity insertion tube 200 to be inserted into a nasal cavity. The fixture 100N according to the sixth embodiment makes contact with the inside of a nasal passage for fixing the nasal cavity insertion tube 200. Specifically, the fixture 100N includes a clip part 110N clipping the bridge of the nose and a connecting part 120N connecting the clip part 110N and the nasal cavity insertion tube 200.

Further, the clip part 110N includes a first insertion portion 111N to be inserted into one nasal passage, a second insertion portion 112N to be inserted into the other nasal passage and a coupling portion 113N coupling the first insertion portion 111N and the second insertion portion 112N. Further, the first insertion portion 111N is a wire that the nasal cavity insertion tube 200N is connected to the tip thereof. In the present embodiment, the first insertion portion 111N as a wire is extended from a nasal passage to the pharynx, and the nasal cavity insertion tube 200N is disposed either on the tip of or in the vicinity of the tip of the first insertion portion 111N. In other words, not the aforementioned nasal cavity insertion tube 200 extended from a nasal passage to the pharynx but a small device functioning enough to expand the pharynx can be used as the nasal cavity insertion tube 200N.

—Seventh Embodiment—

Figure 29:
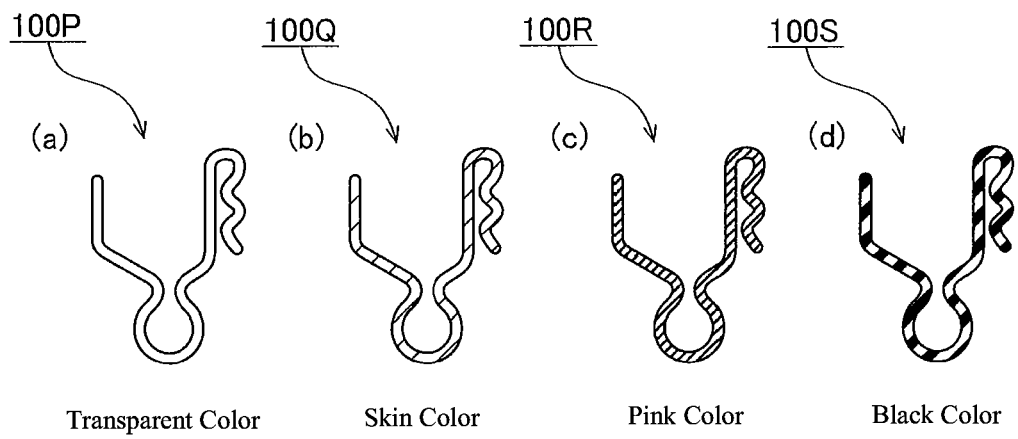
FIG. 29 includes front views of fixtures (with respective colors) according to a seventh embodiment of the present invention.

In the aforementioned embodiments and variations, the colors of the fixtures have not been mentioned. However, so as not to stand out when attached, the color of a fixture 100P may be a transparent color as shown in FIG. 29($a$); the color of a fixture 100Q may be a skin color as shown in FIG. 29($b$); the color of a fixture 100R may be a pink color as shown in FIG. 29($c$); the color of a fixture 100S may be a black color as shown in FIG. 29($d$). The aforementioned various embodiments and variations can be applied to the configurations of the fixtures 100P, 100Q, 100R and 100S.

—Eighth Embodiment—

Figure 30:
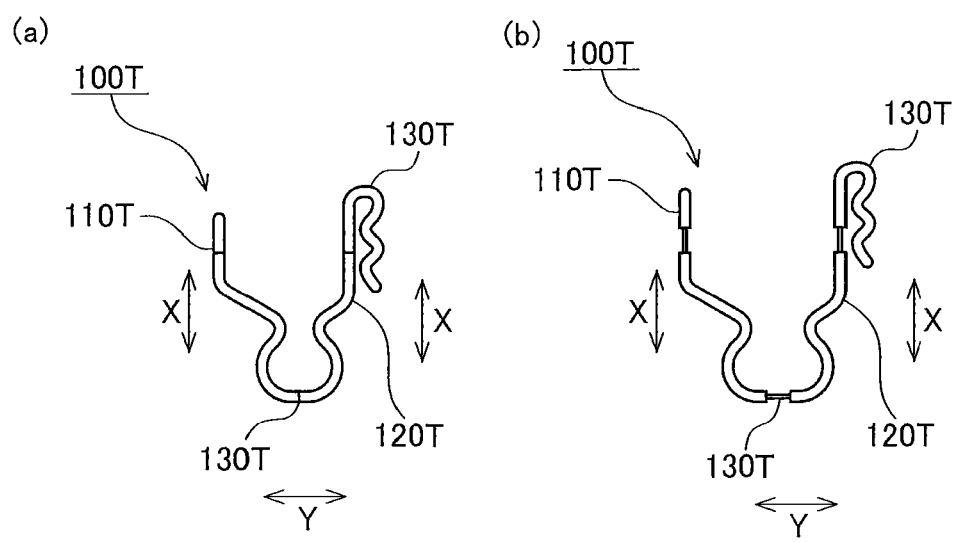
FIG. 30 includes front views of a length adjustable fixture according to an eighth embodiment of the present invention.

In the aforementioned variations (F) and (G) of the first embodiment, the fixtures 100F and 100G having a length adjusting function have been exemplified. However, a fixture 100T shown in FIGS. 30(a) and 30(b) is also in the scope of the present invention.

In other words, the fixture 100T includes a first wire rod part 110T to be inserted into one nasal passage, a second wire rod part 120T to be inserted into the other nasal passage and a third wire rod part 130T holding the nasal cavity insertion tube 200. Further, in the present embodiment, both of the first wire rod part 110T and the second wire rod part 120T can be adjusted in the length thereof with respect to a longitudinal direction (an arrow X direction) . It should be noted that both of the first wire rod part 110T and the second wire rod part 120T are herein configured to be adjustable in the length thereof, but either of the first wire rod part 110T and the second wire rod part 120T may be adjustable in the length thereof. The length adjusting mechanism is similar to the aforementioned variations (F) and (G) of the first embodiment, and therefore, explanation thereof will be omitted.

Further, in the present embodiment, the coupling part 130T between the first wire rod part 110T and the second wire rod part 120T is configured to be adjustable in the length thereof with respect to a width direction (an arrow Y direction). The length adjusting function is also similar to the aforementioned variations (F) and (G) of the first embodiment, and therefore, explanation thereof will be omitted.

In other words, the fixture 100T of the present embodiment is configured to be adjustable in the length thereof in both the longitudinal direction (the arrow X direction) and the width direction (the arrow Y direction). Accordingly, the fixture 100T can be attached in accordance with the nasal size of a patient.

—Ninth Embodiment—

In the aforementioned embodiments, the method of piercing the fixture into the nasal cavity insertion tube has been exemplified as a method of fixing the fixture and the nasal cavity insertion tube. However, the present invention is not limited to this. The fixture 100 and the nasal cavity insertion tube 200 may be fixed by means of the following method. It should be noted that the aforementioned various embodiments and variations can be applied to the fixture 100 and the nasal cavity insertion tube 200.

Figure 31:
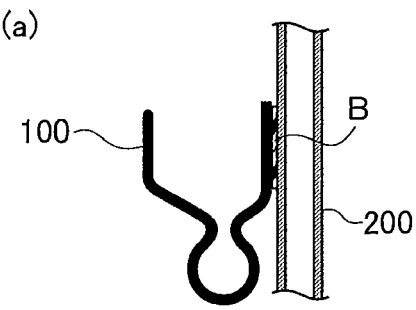
FIG. 31 is a schematic diagram showing a method of connecting a fixture and a nasal cavity insertion tube according to a ninth embodiment of the present invention.
Figure 31:
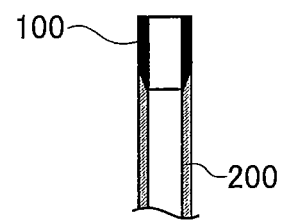
Figure 31:
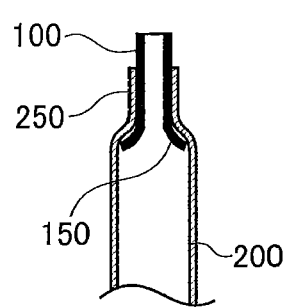
Figure 31:
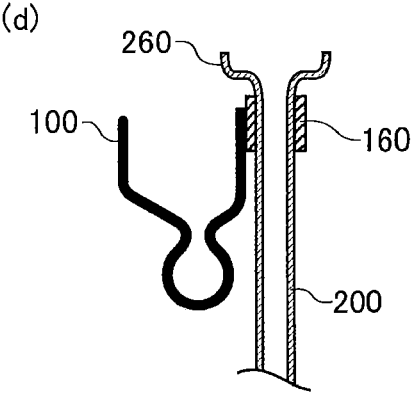

Specifically, as shown in FIG. 31(a), the fixture 100 and the nasal cavity insertion tube 200 may be fixed by means of welding (a welding portion B), or alternatively, may be adhered by means of an adhesive B.

Further, as shown in FIG. 31(b), the fixture 100 and the nasal cavity insertion tube 200 may be fixed by means of a fitting structure.

Further as shown in FIG. 31(c), the fixture 100 may be fixed to the inner peripheral surface of the nasal cavity insertion tube 200. Specifically, the nasal cavity insertion tube 200 has a constricted portion 250 on the base end section thereof. Further, a tip portion 150, having an increased diameter, of the fixture 100 is fitted onto the constricted portion 250. Accordingly, the fixture 100 and the nasal cavity insertion tube 200 are fixed.

Further as shown in FIG. 31(d), the fixture 100 may be fixed to the outer peripheral surface of the nasal cavity insertion tube 200. Specifically, the nasal cavity insertion tube 200 having a flanged portion 260 is inserted through the inside of a tubular structure part 160 attached to the fixture 100. Accordingly, the tubular structure part 160 is received by the flanged portion 260. Thus, the fixture 100 and the nasal cavity insertion tube 200 are fixed.

The fixture and the nasal cavity insertion device set according to the present invention have a feature of preventing the displacement or the detachment of the nasal cavity insertion tube during the sleep of a patient of sleep disorder.

What is claimed is:

1. A nasal cavity insertion device set comprising:
   a nasal cavity insertion device fixture formed of a wire rod; and
   a nasal cavity insertion device having a length roughly the same as a distance from an entrance of a nasal passage to a pharynx and configured to be inserted into the pharynx via a nasal passage and to expand the pharynx, wherein the nasal cavity insertion device fixture has:
   a first wire rod part;
   a second wire rod part connected to the first wire rod part, the second wire rod part being formed by folding back the wire rod so that the second wire rod part is opposed to the first wire rod part; and
   a third wire rod part connected to the second wire rod part, the third wire rod part being formed by bending the wire rod so that the third wire rod part is disposed oppositely to a side of the second wire rod part facing the first wire rod part; and
   a fourth wire rod part connected to the third wire rod part, the fourth wire rod part being formed by folding back the wire rod in a direction opposite the third wire rod part so that the fourth wire rod part is opposed to a side of the third wire rod part that is opposite a side facing the second wire rod part, wherein the first wire rod part and the second wire rod part has:
   first opposed portions separated at a first distance;
   second opposed portions connected to the first opposed portions, the second opposed portions being separated at a second distance shorter than the first distance; and
   third opposed portions connected to the second opposed portions, the third opposed portions being separated at a third distance longer than the second distance, wherein the nasal cavity insertion device comprises:
   a first portion configured to be penetrated by the third wire rod part; and
   a second portion configured to be attached by the second wire rod part and the third wire rod part, the second portion being on an outer surface of the nasal cavity insertion device.

2. The nasal cavity insertion device set according to claim 1, wherein the second wire rod part is provided with a length adjusting portion for adjusting a length of the second wire rod part.

3. The nasal cavity insertion device set according to claim 1, further comprising a resinous coating on the wire rod.

4. The nasal cavity insertion device set according to claim 1, wherein the nasal cavity insertion device has a plurality of holes or thin portions disposed at predetermined intervals, wherein the holes or the thin portions are configured to be penetrated by the third wire rod part.

5. A nasal cavity insertion device fixture formed of a wire rod, the nasal cavity insertion device fixture comprising:
   a first wire rod part;
   a second wire rod part connected to the first wire rod part, the second wire rod part formed by folding back the wire rod so that the second wire rod part is opposed to the first wire rod part;

a third wire rod part connected to the second wire rod part, the third wire rod part formed by bending the wire rod so that the third wire rod part is disposed oppositely to a side of the second wire rod part facing the first wire rod part; and a circular wire rod part disposed oppositely to an end of the first wire rod part connected to the second wire rod part, wherein the second wire rod part is provided with a length adjusting portion for only adjusting a length of the second wire rod part by dividing the second wire rod part into a section continued to the first wire rod part and another section continued to the third wire part, wherein the length adjusting portion comprises:

a convex portion provided at the top of the section continued to the first wire rod part;

a hollow-shaped tube body provided at the tip of the section continued to the third wire rod part in order to enclose the section continued to the first wire rod part; and multiple convex portions provided at predetermined intervals within the tube body.

6. The nasal cavity insertion device fixture according to claim 5, wherein the circular wire rod part is formed along a conceptual plane arranged perpendicularly to the axis of the first wire rod part.

7. A nasal cavity insertion device fixture formed of a wire rod, the nasal cavity insertion device fixture comprising:

a first wire rod part;

a second wire rod part connected to the first wire rod part, the second wire rod part formed by folding back the wire rod so that the second wire rod part is opposed to the first wire rod part;

a third wire rod part connected to the second wire rod part, the third wire rod part formed by bending the wire rod so that the third wire rod part is disposed oppositely to a side of the second wire rod part facing the first wire rod part; and a circular wire rod part disposed oppositely to an end of the first wire rod part connected to the second wire rod part, wherein the entire circumference of the circular wire rod part is included on a conceptual plane in which the second wire rod part and the third wire rod part are included.

8. A nasal cavity insertion tube fixture, comprising:

a first contact part;

a second contact part disposed oppositely to the first contact part;

a coupling portion coupling the first contact part and the second contact part, wherein the first contact part and the second contact part are configured to press a bridge of a nose from both sides to firmly fix the nasal cavity insertion tube fixture and prevent displacement or detachment of a nasal cavity insertion tube from the nose during use, wherein the nasal cavity insertion tube has a first end portion and a second end portion, and wherein the second end portion is opposite to the first end portion; and a connecting part formed on the second contact part and configured to connect a portion near the first end portion of the nasal cavity insertion tube to the second contact part, the nasal cavity insertion tube configured to be inserted into a pharynx via a nasal passage such that the second end portion is directed to the pharynx.

9. The nasal cavity insertion tube fixture according to claim 8, wherein either the first contact part or the second contact part has a plate shape, a tubular shape or a spring shape.

10. A nasal cavity insertion tube set, comprising:

the nasal cavity insertion tube fixture according to claim 8; and the nasal cavity insertion tube of claim 8 to be connected to the connecting part of the nasal cavity insertion tube fixture.

11. A nasal cavity insertion device fixture formed of a wire rod, the nasal cavity insertion device fixture comprising:

a first wire rod part;

a second wire rod part connected to the first wire rod part, the second wire rod part formed by folding back the wire rod so that the second wire rod part is opposed to the first wire rod part;

a third wire rod part connected to the second wire rod part, the third wire rod part formed by bending the wire rod so that the third wire rod part is disposed oppositely to a side of the second wire rod part facing the first wire rod part; and a circular wire rod part disposed oppositely to an end of the first wire rod part connected to the second wire rod part, wherein the second wire rod part is provided with a length adjusting portion for only adjusting a length of the second wire rod part by dividing the second wire rod part into a section continued to the first wire rod part and another section continued to the third wire part, wherein the length adjusting portion comprises:

a male-threaded shaft portion provided on the tip of the section continued to the first wire rod part; and a tube body provided to the tip of the section continued to the third wire rod part, the inside of the tube body is female-threaded.

* * * * *